US009024939B2

(12) United States Patent
Sabiston et al.

(10) Patent No.: US 9,024,939 B2
(45) Date of Patent: May 5, 2015

(54) METHOD AND APPARATUS FOR APPLYING A ROTATIONAL TRANSFORM TO A PORTION OF A THREE-DIMENSIONAL REPRESENTATION OF AN APPLIANCE FOR A LIVING BODY

(75) Inventors: Robert Malcolm Sabiston, Vancouver (CA); Jeffrey David Chang, Vancouver (CA); Christopher Cameron Handford, Vancouver (CA)

(73) Assignee: Vorum Research Corporation (CA)

( * ) Notice: Subject to any disclaimer, the term of this patent is extended or adjusted under 35 U.S.C. 154(b) by 634 days.

(21) Appl. No.: 13/260,134

(22) PCT Filed: Mar. 31, 2009

(86) PCT No.: PCT/CA2009/000417
§ 371 (c)(1),
(2), (4) Date: Sep. 23, 2011

(87) PCT Pub. No.: WO2010/111768
PCT Pub. Date: Oct. 7, 2010

(65) Prior Publication Data
US 2012/0019531 A1    Jan. 26, 2012

(51) Int. Cl.
*G06T 15/00* (2011.01)
*G06T 1/00* (2006.01)
(Continued)

(52) U.S. Cl.
CPC ....... *A61F 2/5046* (2013.01); *A61F 2002/5049* (2013.01); *A61F 2002/505* (2013.01);
(Continued)

(58) Field of Classification Search
CPC .... G06T 13/00; G06T 2210/44; G06T 3/0093
See application file for complete search history.

(56) References Cited

U.S. PATENT DOCUMENTS

| 4,430,718 A | 2/1984 | Hendren |
| 4,436,684 A | 3/1984 | White |

(Continued)

FOREIGN PATENT DOCUMENTS

| CA | 2095238 | 5/1992 |
| CA | 2277093 | 7/1998 |

(Continued)

OTHER PUBLICATIONS

Harvey et al., "A Review of CAD/CAM Procedures for the Production of Custom Made Artificial Hip Joints", IEEE, 1989, pp. 1938-1939.

(Continued)

*Primary Examiner* — James A Thompson
*Assistant Examiner* — Tapas Mazumder
(74) *Attorney, Agent, or Firm* — Kolisch Hartwell, P.C.

(57) ABSTRACT

A method and apparatus for applying a rotational transform to a portion of a three-dimensional representation of an appliance for a living body is disclosed. The representation is defined by an input plurality of coordinates stored in a processor circuit memory, the input plurality of coordinates representing a general shape of the appliance. The method involves applying the rotational transform to the portion of the representation of the appliance within the transform volume to produce an output plurality of coordinates representing a modified shape of the appliance such that the general shape of portions of the appliance outside the transform volume remain un-modified by the rotational transform, and storing the output plurality of coordinates in the processor circuit memory.

39 Claims, 11 Drawing Sheets

(51) Int. Cl.
| | |
|---|---|
| *G06F 17/00* | (2006.01) |
| *G09G 5/00* | (2006.01) |
| *A61F 2/50* | (2006.01) |
| *G05B 19/4099* | (2006.01) |
| *G06T 19/20* | (2011.01) |

(52) U.S. Cl.
CPC .. *G05B19/4099* (2013.01); *G05B 2219/35134* (2013.01); *G06T 19/20* (2013.01); *G06T 2219/2016* (2013.01); *A61F 2002/5047* (2013.01); *G05B 2219/45168* (2013.01)

(56) References Cited

U.S. PATENT DOCUMENTS

| | | | |
|---|---|---|---|
| 4,575,805 A | | 3/1986 | Moermann et al. |
| 4,629,409 A | | 12/1986 | Satoh et al. |
| 4,663,720 A | | 5/1987 | Duret et al. |
| 4,769,638 A | * | 9/1988 | Woolfolk ............... 345/111 |
| 4,912,644 A | | 3/1990 | Aoyama et al. |
| 5,056,204 A | | 10/1991 | Bartschi |
| 5,224,049 A | | 6/1993 | Mushabac |
| 5,360,446 A | | 11/1994 | Kennedy |
| 5,452,219 A | | 9/1995 | Dehoff et al. |
| 5,475,613 A | | 12/1995 | Itoga et al. |
| 5,506,785 A | | 4/1996 | Blank et al. |
| 5,510,066 A | | 4/1996 | Fink et al. |
| 5,539,649 A | | 7/1996 | Walsh et al. |
| 5,543,103 A | | 8/1996 | Hogan et al. |
| 5,742,511 A | | 4/1998 | Chasse et al. |
| 5,778,177 A | | 7/1998 | Azar |
| 6,108,006 A | | 8/2000 | Hoppe |
| 6,212,441 B1 | | 4/2001 | Hazama et al. |
| 6,389,375 B1 | | 5/2002 | Thomsen et al. |
| 6,463,351 B1 | | 10/2002 | Clynch |
| 6,473,667 B1 | | 10/2002 | Lee |
| 6,701,200 B1 | | 3/2004 | Lukis et al. |
| 6,772,026 B2 | | 8/2004 | Bradbury et al. |
| 6,839,607 B2 | | 1/2005 | Wooten |
| 6,920,414 B2 | | 7/2005 | Topholm |
| 6,982,710 B2 | | 1/2006 | Salomie |
| 7,134,874 B2 | | 11/2006 | Chishti et al. |
| 7,167,189 B2 | | 1/2007 | Di Lelle et al. |
| 7,221,380 B2 | | 5/2007 | Hunter et al. |
| 7,299,101 B2 | | 11/2007 | Lukis et al. |
| 7,435,083 B2 | | 10/2008 | Chishti et al. |
| 8,116,900 B2 | | 2/2012 | Slemker et al. |
| 2001/0000805 A1 | | 5/2001 | Kadono |
| 2001/0002232 A1 | | 5/2001 | Young et al. |
| 2001/0002310 A1 | | 5/2001 | Chishti et al. |
| 2001/0025203 A1 | | 9/2001 | Gervasi |
| 2002/0013636 A1 | | 1/2002 | O'Brien et al. |
| 2002/0024521 A1 | * | 2/2002 | Goden ............... 345/474 |
| 2002/0149137 A1 | | 10/2002 | Jang et al. |
| 2003/0195623 A1 | | 10/2003 | Marchitto et al. |
| 2003/0204279 A1 | | 10/2003 | Yokohari et al. |
| 2003/0206820 A1 | | 11/2003 | Keicher et al. |
| 2004/0068337 A1 | | 4/2004 | Watson et al. |
| 2004/0085311 A1 | | 5/2004 | Lee et al. |
| 2004/0164957 A1 | * | 8/2004 | Yamaguchi et al. ......... 345/156 |
| 2005/0043837 A1 | | 2/2005 | Rubbert et al. |
| 2005/0089213 A1 | | 4/2005 | Geng |
| 2005/0089822 A1 | | 4/2005 | Geng |
| 2005/0119777 A1 | | 6/2005 | Argogast et al. |
| 2005/0286798 A1 | | 12/2005 | Pollard et al. |
| 2006/0094951 A1 | | 5/2006 | Dean et al. |
| 2006/0100832 A1 | | 5/2006 | Bowman |
| 2006/0203010 A1 | | 9/2006 | Kirchner et al. |
| 2006/0286501 A1 | | 12/2006 | Chishti et al. |
| 2007/0118243 A1 | | 5/2007 | Schroeder et al. |
| 2009/0248184 A1 | | 10/2009 | Steingart et al. |
| 2009/0306801 A1 | | 12/2009 | Sivak et al. |
| 2013/0127833 A1 | * | 5/2013 | Davidson ............... 345/419 |

FOREIGN PATENT DOCUMENTS

| | | |
|---|---|---|
| CA | 2405738 | 10/2001 |
| EP | 1273876 A2 | 1/2003 |
| FR | 2855959 | 12/2004 |
| FR | 2885518 | 11/2006 |
| GB | 2266214 A | 10/1993 |
| JP | 2003299679 | 10/2003 |
| WO | 8911257 | 11/1989 |
| WO | 92/08175 A1 | 5/1992 |
| WO | 9718533 A1 | 5/1997 |
| WO | 02/34157 A2 | 5/2002 |
| WO | 2004100045 A1 | 11/2004 |
| WO | 2006110895 | 10/2006 |
| WO | 2009015455 | 2/2009 |
| WO | WO2009052602 * | 4/2009 |

OTHER PUBLICATIONS

Oberg, K et al. "The CAPOD System—A Scandinavian CAD CAM System for Prosthetic Sockets", Journal of Prosthetics and Orthotics, 1989, vol. 1, No. 3, pp. 139-148.

He et al., "A PC-based ultrasound scanning system for imaging a residual limb", Proceedings of the 16th Annual International Conference of the IEEE Engineering in Medicine and Biology Society, 1994, Baltimore, MD Nov. 3-6, 1994, pp. 480-481, vol. 1, ISBN: 0-7803-2050-6.

Jensen, Nielsen, K, "Bio-Surfaces and Geometric References for a Standardized Biomechanical Design Methodology for Mass Customization", Ph.D. thesis, Brigham Young University, Apr. 2008, pp. 1-136.

International Search Report dated Jun. 18, 2008 in connection with related PCT Application No. PCT/CA2007/001884.

Anonymous, "CANFIT-PLUSTM P&O Design", posted on the Internet on Oct. 15, 2006 and accessed Jun. 19, 2008 at http:\\web.archive.org/web/20061015183514/www.vorum.com/P&O_System/prod_P&OSystem_P&O_Design.asp?pageID=28.

International Search Report dated Apr. 9, 2009 in connection with related PCT Application No. PCT/CA2008/001362.

International Search Report dated Dec. 9, 2009 in connection with related PCT Application No. PCT/CA2009/000417.

US Receiving Office, International Search Report dated Apr. 17, 2008 in connection with related International Application No. PCT/CA2007/001337, 2 pgs.

A.L. Darling and W. Sun, "Orthotic design through 3D reconstruction: A passive-assistance ankle-foot orthotic", Applied Bionics and Biomechanics, Cambridge, Woodhead Publishing Ltd., vol. 3, No. 2, Jan. 1, 2006, pp. 93-99.

European Patent Office, Supplementary European Search Report and Written Opinion dated Mar. 26, 2012 in connection with related Application No. EP-21047017, 6 pgs.

Michael W. Vannier et al., "Visualization of Prosthesis Fit in Lower-Limb Amputees", IEEE Computer Graphics and Applications, Sep./Oct. 1997, pp. 16-29.

European Patent Office, "Supplementary European Search Report" in connection with related European Patent App. No. 08783275.4, dated Nov. 6, 2013, 7 pages.

M.E. Riechmann et al., "Computer-Aided Design and Computer-Aided Manufacturing of Below-Knee Prosthetics", Proceedings of the 1991 IEEE Seventeenth Annual Northeast Bioengineering Conference, Apr. 4-5, 1991, 4 pages.

European Patent Office, "Extended European Search Report" in connection with related European Patent Application No. 09842459.1, dated Jul. 8, 2014, 7 pages.

* cited by examiner

METHOD AND APPARATUS FOR APPLYING A ROTATIONAL TRANSFORM TO A PORTION OF A THREE-DIMENSIONAL REPRESENTATION OF AN APPLIANCE FOR A LIVING BODY

BACKGROUND OF THE INVENTION

1. Field of Invention

This invention relates generally to three-dimensional shape representations and more particularly to applying a rotational transformation to a portion of a representation of an appliance for a living body.

2. Description of Related Art

Prostheses, orthoses, and other support appliances are commonly produced from three-dimensional representations of a body part of a human or an animal. The three-dimensional representation may then be manipulated on a computer using a three-dimensional shape editing program to produce a modified representation of the body part. The modified representation may be used to generate instructions for controlling a carving machine that is configured to directly produce an appliance, or to produce a mold for making an appliance, for example. An orthosis is an appliance that is applied externally to a body part to correct deformity, improve function, or relieve symptoms of a disease by supporting or assisting the musculo-neuro-skeletal system. A prosthesis is an appliance that replaces a missing body part. Other appliances such as supporting seats or standing shells for supporting the body of a person having limited mobility may also be produced from modified representations of body parts.

The three-dimensional representation of the body part may be produced using a non-contact optical scanner that images the body part with a high level of accuracy. The scanner may include a laser for illuminating the body part with structured light and a video camera for capturing images of the illuminated body part. The captured images may then be processed to extract coordinates of the surface of the body part, which may be used as input coordinates to a computer for producing a preliminary three-dimensional representation of the appliance. In cases where scanned input coordinates are available for the specific patient for whom the appliance is to be produced, it is common to make certain modifications to the scanned coordinates to provide compression and/or relief such that the final appliance provides the required support where needed while being sufficiently comfortable for the patient. In other cases, the preliminary three-dimensional representation of the appliance may be provided from a library of body parts, which may require modifications in size and shape to provide the required support and comfort for the patient.

There remains a need for methods and apparatus for modifying a set of input coordinates representing a preliminary shape of an appliance to produce a modified set of coordinates representing a final shape of the appliance.

SUMMARY OF THE INVENTION

In accordance with one aspect of the invention there is provided a method for applying a rotational transform to a portion of a three-dimensional representation of an appliance for a living body, the representation being defined by an input plurality of coordinates stored in a processor circuit memory, the input plurality of coordinates representing a general shape of the appliance. The method involves receiving operator input identifying a coordinate location of a rotational axis about which the rotational transform is to be applied, receiving operator input of at least one constraint defining an extent of a transform volume within which the rotational transform is to be applied to the representation of the appliance, and receiving operator input of a rotational transform magnitude. The method also involves applying the rotational transform to the portion of the representation of the appliance within the transform volume to produce an output plurality of coordinates representing a modified shape of the appliance such that the general shape of portions of the appliance outside the transform volume remain unmodified by the rotational transform, and storing the output plurality of coordinates in the processor circuit memory.

The method may involve generating a set of instructions operable to control a computer aided manufacturing machine to produce one of the appliance and a mold for producing the appliance in accordance with the output plurality of coordinates.

The method may involve generating display signals operable to cause a representation of the output plurality of coordinates to be displayed on a display associate with the processor circuit.

Receiving the operator input of the at least one constraint may involve receiving operator input of at least one axial constraint limiting an extent of the transform volume in a direction along the rotational axis.

Receiving the operator input defining the at least one axial constraint may involve receiving operator input defining at least one constraint plane oriented orthogonal to the rotational axis and intersecting the appliance representation.

Receiving the operator input defining the at least one axial constraint may involve receiving operator input defining first and second spaced apart axial constraints along the rotational axis, the first and second axial constraints limiting an extent of the transform volume to between the first and second axial constraints.

The method may involve identifying an axial blending region extending into the transform volume from the at least one axial constraint, and applying the rotational transform may involve reducing a magnitude of the rotational transform within the axial blending region to cause continuity of shape between modified portions of the representation of the appliance within the transform volume and un-modified portions of the representation of the appliance outside the transform volume.

Reducing the magnitude of the rotational transform may involve applying a rotational transform having substantially zero magnitude at the axial constraint, and a magnitude that progressively increases with distance away from the at least one axial constraint to reach a full rotational transform magnitude beyond the axial blending region.

Identifying the axial blending region may involve receiving operator input of a distance defining an extent of the blending region into the transform volume.

Receiving the operator input of the at least one constraint may involve receiving operator input of first and second rotational constraints with respect to the rotational axis, the first and second rotational constraints defining an angular extent of the transform volume about the rotational axis.

Applying the rotational transform to the portion of the three-dimensional representation of the appliance within the transform volume may involve identifying first and second rotational blending regions extending from the first and second rotational constraints into the transform volume, and applying the rotational transform may involve reducing a magnitude of the rotational transform within the first and second rotational blending regions respectively to cause continuity of shape between modified portions of the representation of the appliance within the transform volume and unmodified portions of the representation of the appliance outside the transform volume.

Reducing the magnitude of the rotational transform may involve applying a rotational transform having substantially zero magnitude at the first and second rotational constraints, and a magnitude that progressively increases with rotational displacement into the transform volume to reach a full rotational transform magnitude beyond the first and second rotational blending regions respectively.

Identifying the first and second rotational blending regions may involve receiving operator input defining a rotational extent of the first and second rotational blending regions into the transform volume.

Identifying the first and second rotational blending regions may involve receiving operator input of a no-blending zone located between the first and second rotational constraints, the no-blending zone defining an angular extent of the transform volume about the rotational axis within which a full magnitude of the rotational transform is to be to be applied, and where the first and second rotational blending regions respectively include portions of the transform volume outside the no-blending zone.

The method may involve receiving operator input of a desired rotational magnitude and direction of the rotational transform to be applied to the portion of the three-dimensional representation of the appliance within the transform volume.

The method may involve defining a reference plane oriented orthogonal to the rotational axis and intersecting the appliance representation, displaying a two-dimensional view of an intersection between the three-dimensional representation of the appliance and the reference plane, and receiving the operator input of the desired magnitude and direction of the rotational transform to be applied may involve receiving an operator selection of a reference point on the reference plane and receiving operator input of a desired rotational displacement of the reference point.

The method may involve displaying a modified shape of the intersection in the two-dimensional view.

Applying the rotational transform may involve for each input coordinate in the input plurality of coordinates determining an angular displacement to be applied to the input coordinate, and generating a rotational transformation matrix for the input coordinate, the rotational transform matrix including elements operable to transform the input coordinate into an output coordinate that may be angularly displaced from the input coordinate by the angular displacement about the rotational axis.

The input plurality of coordinates may be defined in a first Cartesian coordinate system and the method may further involve generating a modeling matrix having elements operable to transform input coordinates between the first coordinate system and a second Cartesian coordinate system, the second coordinate system having an origin located on the rotational axis, a first axis aligned with the rotational axis, and second and third axes orthogonal to the rotational axis. Determining the angular displacement may involve determining a corresponding coordinate of the input coordinate in the second coordinate system, and determining an angular displacement of each the corresponding coordinate within a plane defined by the second and third axes of the second coordinate system.

Receiving operator input identifying the coordinate location of the rotational axis may involve receiving operator input defining coordinates of a three-dimensional line representing a location of the rotational axis with respect to the appliance representation, a location of a reference plane intersecting the appliance representation and oriented orthogonal to the three-dimensional line, and a location of an origin point on the reference plane through which the rotational axis passes.

The method may involve displaying a three-dimensional representation of the appliance, the reference plane, and the three-dimensional line and receiving the operator input may involve receiving pointer signals from a pointing device in communication with the processor circuit, the pointing signals being operable to define desired changes to the coordinates of at least one of the three-dimensional line, the location of the reference plane, and the location of the origin point on the reference plane with respect to the appliance.

The method may involve displaying a two-dimensional view of the intersection of the general shape of the appliance with the reference plane and receiving the operator input may involve receiving pointer signals from the pointing device, the pointing signals being operable to define desired changes to the origin point on the reference plane.

Applying the rotational transform to the portion of the three-dimensional representation of the appliance within the transform volume to produce an output plurality of coordinates may involve producing modified coordinates representing the modified shape of the appliance within the transform volume, and re-sampling the modified coordinates and the un-modified coordinates outside the transform volume to produce the output plurality of coordinates representing the modified appliance representation.

In accordance with another aspect of the invention there is provided an apparatus for applying a rotational transform to a portion of a three-dimensional representation of an appliance for a living body, the representation being defined by an input plurality of coordinates, the input plurality of coordinates representing a general shape of the appliance. The apparatus includes a processor circuit operably configured to receive operator input identifying a coordinate location of a rotational axis about which the rotational transform is to be applied, to receive operator input of at least one constraint defining an extent of a transform volume within which the rotational transform is to be applied to the representation of the appliance, and to receive operator input of a rotational transform magnitude. The processor circuit is also operably configured to apply the rotational transform to the portion of the representation of the appliance within the transform volume to produce an output plurality of coordinates representing a modified shape of the appliance such that the general shape of portions of the appliance outside the transform volume remain un-modified by the rotational transform, and to store the output plurality of coordinates in a memory of the processor circuit.

The processor circuit may be operably configured to generate a set of instructions operable to control a computer aided manufacturing machine to produce one of the appliance and a mold for producing the appliance in accordance with the output plurality of coordinates.

The processor circuit may be operably configured to generate display signals operable to cause a representation of the output plurality of coordinates to be displayed.

The processor circuit may be operably configured to generate display signals operable to cause a representation of the output plurality of coordinates to be displayed.

The processor circuit may be operably configured to receive the operator input of the at least one constraint by receiving operator input of at least one axial constraint limiting an extent of the transform volume in a direction along the rotational axis.

The processor circuit may be operably configured to receive the operator input defining the at least one axial constraint by receiving operator input defining at least one constraint plane oriented orthogonal to the rotational axis and intersecting the appliance representation.

The processor circuit may be operably configured to receive the operator input defining the at least one axial constraint by receiving operator input defining first and second spaced apart axial constraints along the rotational axis, the first and second axial constraints limiting an extent of the transform volume to between the first and second axial constraints.

The processor circuit may be operably configured to identify an axial blending region extending into the transform volume from the at least one axial constraint, and the processor circuit may be operably configured to apply the rotational transform by reducing a magnitude of the rotational transform within the axial blending region to cause continuity of shape between modified portions of the representation of the appliance within the transform volume and un-modified portions of the representation of the appliance outside the transform volume.

The processor circuit may be operably configured to reduce the magnitude of the rotational transform by applying a rotational transform having substantially zero magnitude at the axial constraint, and a magnitude that progressively increases with distance away from the at least one axial constraint to reach a full rotational transform magnitude beyond the axial blending region.

The processor circuit may be operably configured to identify the axial blending region by receiving operator input of a distance defining an extent of the blending region into the transform volume.

The processor circuit may be operably configured to receive the operator input of the at least one constraint by receiving operator input of first and second rotational constraints with respect to the rotational axis, the first and second rotational constraints defining an angular extent of the transform volume about the rotational axis.

The processor circuit may be operably configured to apply the rotational transform to the portion of the three-dimensional representation of the appliance within the transform volume by identifying first and second rotational blending regions extending from the first and second rotational constraints into the transform volume, and the processor circuit may be operably configured to apply the rotational transform by reducing a magnitude of the rotational transform within the first and second rotational blending regions respectively to cause continuity of shape between modified portions of the representation of the appliance within the transform volume and unmodified portions of the representation of the appliance outside the transform volume.

The processor circuit may be operably configured to reduce the magnitude of the rotational transform by applying a rotational transform having substantially zero magnitude at the first and second rotational constraints, and a magnitude that progressively increases with rotational displacement into the transform volume to reach a full rotational transform magnitude beyond the first and second rotational blending regions respectively.

The processor circuit may be operably configured to identify the first and second rotational blending regions by receiving operator input defining a rotational extent of the first and second rotational blending regions into the transform volume.

The processor circuit may be operably configured to identify the first and second rotational blending regions by receiving operator input of a no-blending zone located between the first and second rotational constraints, the no-blending zone defining an angular extent of the transform volume about the rotational axis within which a full magnitude of the rotational transform is to be applied, and the first and second rotational blending regions respectively may include portions of the transform volume outside the no-blending zone.

The processor circuit may be operably configured to receive operator input of a desired rotational magnitude and direction of the rotational transform to be applied to the portion of the three-dimensional representation of the appliance within the transform volume.

The processor circuit may be operably configured to define a reference plane oriented orthogonal to the rotational axis and intersecting the appliance representation, to display a two-dimensional view of an intersection between the three dimensional representation of the appliance and the reference plane, and the processor circuit may be operably configured to receive the operator input of the desired magnitude and direction of the rotational transform to be applied by receiving an operator selection of a reference point on the reference plane, and receiving operator input of a desired rotational displacement of the reference point.

The processor circuit may be operably configured to display a modified shape of the intersection in the two-dimensional view.

The processor circuit may be operably configured to apply the rotational transform by determining an angular displacement to be applied to each input coordinate in the input plurality of coordinates, and generating a rotational transformation matrix for the input coordinate, the rotational transform matrix including elements operable to transform the input coordinate into an output coordinate that is angularly displaced from the input coordinate by the angular displacement about the rotational axis.

The input plurality of coordinates may be defined in a first Cartesian coordinate system and the processor circuit may be operably configured to generate a modeling matrix having elements operable to transform input coordinates between the first coordinate system and a second Cartesian coordinate system, the second coordinate system having an origin located on the rotational axis, a first axis aligned with the rotational axis, and second and third axes orthogonal to the rotational axis, and the processor circuit may be operably configured to determine the angular displacement by determining a corresponding coordinate of the input coordinate in the second coordinate system, and determining an angular displacement of each the corresponding coordinate within a plane defined by the second and third axes of the second coordinate system.

The processor circuit may be operably configured to receive operator input identifying the coordinate location of the rotational axis by receiving operator input defining coordinates of a three-dimensional line representing a location of the rotational axis with respect to the appliance representation, a location of a reference plane intersecting the appliance representation and oriented orthogonal to the three-dimensional line, and a location of an origin point on the reference plane through which the rotational axis passes.

The processor circuit may be operably configured to display a three-dimensional representation of the appliance, the reference plane, and the three-dimensional line and the processor circuit may be operably configured to receive the operator input by receiving pointer signals from a pointing device in communication with the processor circuit, the pointing signals being operable to define desired changes to the coordinates of at least one of the three-dimensional line, the location of the reference plane, and the location of the origin point on the reference plane with respect to the appliance.

The processor circuit may be operably configured to display a two-dimensional view of the intersection of the general shape of the appliance with the reference plane and the processor circuit may be operably configured to receive the operator input by receiving pointer signals from the pointing device, the pointing signals being operable to define desired changes to the origin point on the reference plane.

The processor circuit may be operably configured to apply the rotational transform to the portion of the three-dimensional representation of the appliance within the transform volume to produce an output plurality of coordinates by producing modified coordinates representing the modified shape of the appliance within the transform volume, and re-sampling the modified coordinates and the un-modified coordinates outside the transform volume to produce the output plurality of coordinates representing the modified appliance representation.

In accordance with another aspect of the invention there is provided a computer readable medium encoded with codes for directing a processor circuit to apply a rotational transform to a portion of a three-dimensional representation of an appliance for a living body, the representation being defined by an input plurality of coordinates stored in a processor circuit memory, the input plurality of coordinates representing a general shape of the appliance. The codes direct the processor circuit to receive operator input identifying a coordinate location of a rotational axis about which the rotational transform is to be applied, and to receive operator input of at least one constraint defining an extent of a transform volume within which the rotational transform is to be applied to the representation of the appliance, and to receive operator input of a rotational transform magnitude. The codes also direct the processor circuit to apply the rotational transform to the portion of the representation of the appliance within the transform volume to produce an output plurality of coordinates representing a modified shape of the appliance such that the general shape of portions of the appliance outside the transform volume remain un-modified by the rotational transform, and to store the output plurality of coordinates in a memory of the processor circuit.

In accordance with another aspect of the invention there is provided a computer readable signal encoded with codes for directing a processor circuit to apply a rotational transform to a portion of a three-dimensional representation of an appliance for a living body, the representation being defined by an input plurality of coordinates stored in a processor circuit memory, the input plurality of coordinates representing a general shape of the appliance. The codes direct the processor circuit to receive operator input identifying a coordinate location of a rotational axis about which the rotational transform is to be applied, and to receive operator input of at least one constraint defining an extent of a transform volume within which the rotational transform is to be applied to the representation of the appliance, and to receive operator input of a rotational transform magnitude. The codes also direct the processor circuit to apply the rotational transform to the portion of the representation of the appliance within the transform volume to produce an output plurality of coordinates representing a modified shape of the appliance such that the general shape of portions of the appliance outside the transform volume remain un-modified by the rotational transform, and to store the output plurality of coordinates in a memory of the processor circuit.

In accordance with another aspect of the invention there is provided an apparatus for applying a rotational transform to a portion of a three-dimensional representation of an appliance for a living body, the representation being defined by an input plurality of coordinates stored in a processor circuit memory, the input plurality of coordinates representing a general shape of the appliance. The apparatus includes provisions for receiving operator input identifying a coordinate location of a rotational axis about which the rotational transform is to be applied, provisions for receiving operator input of at least one constraint defining an extent of a transform volume within which the rotational transform is to be applied to the representation of the appliance, and provisions for receiving operator input of a rotational transform magnitude. The apparatus also includes provisions for applying the rotational transform to the portion of the representation of the appliance within the transform volume to produce an output plurality of coordinates representing a modified shape of the appliance such that the general shape of portions of the appliance outside the transform volume remain un-modified by the rotational transform, and provisions for storing the output plurality of coordinates in the processor circuit memory.

The apparatus may include provisions for generating a set of instructions operable to control a computer aided manufacturing machine to produce one of the appliance and a mold for producing the appliance in accordance with the output plurality of coordinates.

The apparatus may include provisions for generating display signals operable to cause a representation of the output plurality of coordinates to be displayed on a display associate with the processor circuit.

The provisions for receiving the operator input of the at least one constraint may include provisions for receiving operator input of at least one axial constraint limiting an extent of the transform volume in a direction along the rotational axis.

The provisions for receiving the operator input defining the at least one axial constraint may include provisions for receiving operator input defining at least one constraint plane oriented orthogonal to the rotational axis and intersecting the appliance representation.

The provisions for receiving the operator input defining the at least one axial constraint may include provisions for receiving operator input defining first and second spaced apart axial constraints along the rotational axis, the first and second axial constraints limiting an extent of the transform volume to between the first and second axial constraints.

The apparatus may include provisions for identifying an axial blending region extending into the transform volume from the at least one axial constraint, and the provisions for applying the rotational transform may include provisions for reducing a magnitude of the rotational transform within the axial blending region to cause continuity of shape between modified portions of the representation of the appliance within the transform volume and un-modified portions of the representation of the appliance outside the transform volume.

The provisions for reducing the magnitude of the rotational transform may include provisions for applying a rotational transform having substantially zero magnitude at the axial constraint, and a magnitude that progressively increases with distance away from the at least one axial constraint to reach a full rotational transform magnitude beyond the axial blending region.

The provisions for identifying the axial blending region may include provisions for receiving operator input of a distance defining an extent of the blending region into the transform volume.

The provisions for receiving the operator input of the at least one constraint may include provisions for receiving operator input of first and second rotational constraints with respect to the rotational axis, the first and second rotational constraints defining an angular extent of the transform volume about the rotational axis.

The provisions for applying the rotational transform to the portion of the three-dimensional representation of the appliance within the transform volume may include provisions for identifying first and second rotational blending regions extending from the first and second rotational constraints into the transform volume, and the provisions for applying the rotational transform may include provisions for reducing a magnitude of the rotational transform within the first and second rotational blending regions respectively to cause continuity of shape between modified portions of the representation of the appliance within the transform volume and unmodified portions of the representation of the appliance outside the transform volume.

The provisions for reducing the magnitude of the rotational transform may include provisions for applying a rotational transform having substantially zero magnitude at the first and second rotational constraints, and a magnitude that progressively increases with rotational displacement into the transform volume to reach a full rotational transform magnitude beyond the first and second rotational blending regions respectively.

The provisions for identifying the first and second rotational blending regions may include provisions for receiving operator input defining a rotational extent of the first and second rotational blending regions into the transform volume.

The provisions for identifying the first and second rotational blending regions may include provisions for receiving operator input of a no-blending zone located between the first and second rotational constraints, the no-blending zone defining an angular extent of the transform volume about the rotational axis within which a full magnitude of the rotational transform is to be applied, and the first and second rotational blending regions respectively may include portions of the transform volume outside the no-blending zone.

The apparatus may include provisions for receiving operator input of a desired rotational magnitude and direction of the rotational transform to be applied to the portion of the three-dimensional representation of the appliance within the transform volume.

The apparatus may include provisions for defining a reference plane oriented orthogonal to the rotational axis and intersecting the appliance representation, provisions for displaying a two-dimensional view of an intersection between the three dimensional representation of the appliance and the reference plane, wherein the provisions for receiving the operator input of the desired magnitude and direction of the rotational transform to be applied may include provisions for receiving an operator selection of a reference point on the reference plane, and provisions for receiving operator input of a desired rotational displacement of the reference point.

The apparatus may include provisions for displaying a modified shape of the intersection in the two-dimensional view.

The provisions for applying the rotational transform may include provisions for determining an angular displacement to be applied to each input coordinate in the input plurality of coordinates, and provisions for generating a rotational transformation matrix for the input coordinate, the rotational transform matrix including elements operable to transform the input coordinate into an output coordinate that may be angularly displaced from the input coordinate by the angular displacement about the rotational axis.

The input plurality of coordinates may be defined in a first Cartesian coordinate system and may further include provisions for generating a modeling matrix having elements operable to transform input coordinates between the first coordinate system and a second Cartesian coordinate system, the second coordinate system having an origin located on the rotational axis, a first axis aligned with the rotational axis, and second and third axes orthogonal to the rotational axis, and the provisions for determining the angular displacement may include provisions for determining a corresponding coordinate of the input coordinate in the second coordinate system, and provisions for determining an angular displacement of each the corresponding coordinate within a plane defined by the second and third axes of the second coordinate system.

The provisions for receiving operator input identifying the coordinate location of the rotational axis may include provisions for receiving operator input defining coordinates of a three-dimensional line representing a location of the rotational axis with respect to the appliance representation, a location of a reference plane intersecting the appliance representation and oriented orthogonal to the three-dimensional line, and a location of an origin point on the reference plane through which the rotational axis passes.

The apparatus may include provisions for displaying a three-dimensional representation of the appliance, the reference plane, and the three-dimensional line and the provisions for receiving the operator input may include provisions for receiving pointer signals from a pointing device in communication with the processor circuit, the pointing signals being operable to define desired changes to the coordinates of at least one of the three-dimensional line, the location of the reference plane, and the location of the origin point on the reference plane with respect to the appliance.

The apparatus may include provisions for displaying a two-dimensional view of the intersection of the general shape of the appliance with the reference plane and the provisions for receiving the operator input may include provisions for receiving pointer signals from the pointing device, the pointing signals being operable to define desired changes to the origin point on the reference plane.

The provisions for applying the rotational transform to the portion of the three-dimensional representation of the appliance within the transform volume to produce an output plurality of coordinates may include provisions for producing modified coordinates representing the modified shape of the appliance within the transform volume, and provisions for re-sampling the modified coordinates and the un-modified coordinates outside the transform volume to produce the output plurality of coordinates representing the modified appliance representation.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

System Overview

Figure 1:
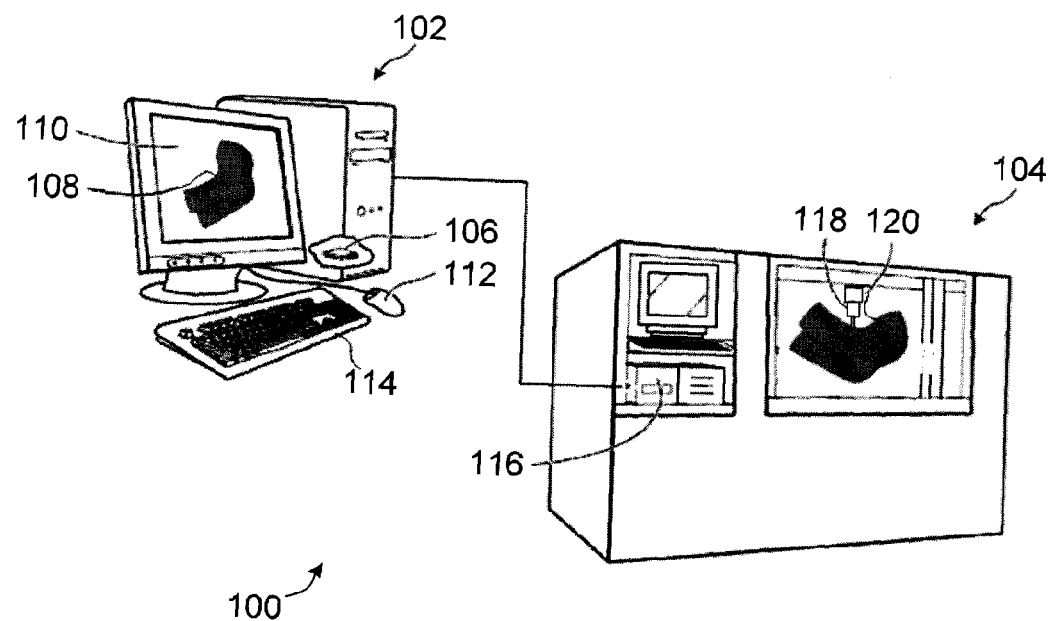
FIG. 1 is a perspective view of a CAD\CAM system for producing an appliance for a living body in accordance with one embodiment of the invention.

Referring to FIG. 1, a CAD\CAM system for producing an appliance for a living body is shown generally at 100. The system 100 includes a computer aided design (CAD) apparatus 102 and a computer aided manufacturing (CAM) machine 104.

The CAD apparatus 102 includes a processor circuit 106, which is operably configured to apply a rotational transform to a portion of a three-dimensional representation 108, f an appliance for a living body. The three-dimensional representation 108 is defined by an input plurality of coordinates representing a general shape of the appliance to be produced from the representation 108. The apparatus 102 also includes a display 110, which is in communication with the processor circuit 106. In the embodiment shown the apparatus 102 also includes a pointing device 112 having one or more actuator buttons (not shown) for receiving operator input from an operator of the apparatus. The apparatus 102 also includes a keyboard 114 for receiving alphanumeric input from the operator. The processor circuit 106 produces signals for causing the display 110 to display a representation of a surface of the appliance being produced. The representation 108 displayed on the display 110 provides interactive visual feedback during modification of the appliance by an operator in response to operator inputs received at the pointing device 112 and the keyboard 114.

In general, producing an appliance for a patient involves receiving the input plurality of coordinates, which define a preliminary representation of the surface of the appliance. The preliminary representation of the appliance is then transformed through various modifications to the general shape of the appliance to produce a final appliance representation. Such modifications may include modifications to the shape of surfaces, such as compressions in areas of the body that tolerate pressure and/or relief in certain other areas of the body that are sensitive to pressure, thus providing a comfortably fitting appliance for the patient. The effects of the modifications on the general shape of the appliance displayed on the display 110 to facilitate review of the modified shape prior to production of the final appliance.

In this embodiment, the CAM machine 104 includes a controller 116 and a machine tool portion 118 for machining the appliance. The controller 116 is in communication with the CAD apparatus 102 for receiving a signal encoded with data representing the modified appliance to be produced. The controller 116 transforms the data into carving instructions operable to control the CAM machine 104 to produce a machined appliance 120. In this embodiment the machined appliance 120 is a mold which is subsequently used to produce a final appliance by molding a thermoplastic or other material over the mold. However in other embodiments final appliance may be machined directly by the CAM machine 104, without the need to produce a mold.

In other embodiments the CAD apparatus 102 may be operably configured to produce an output file including carving instructions for controlling the CAM machine 104. The output file may be transferred to the CAM machine 104 through a communication link or a computer readable medium such as a CDROM disk or flash drive, for example.

Figure 2:
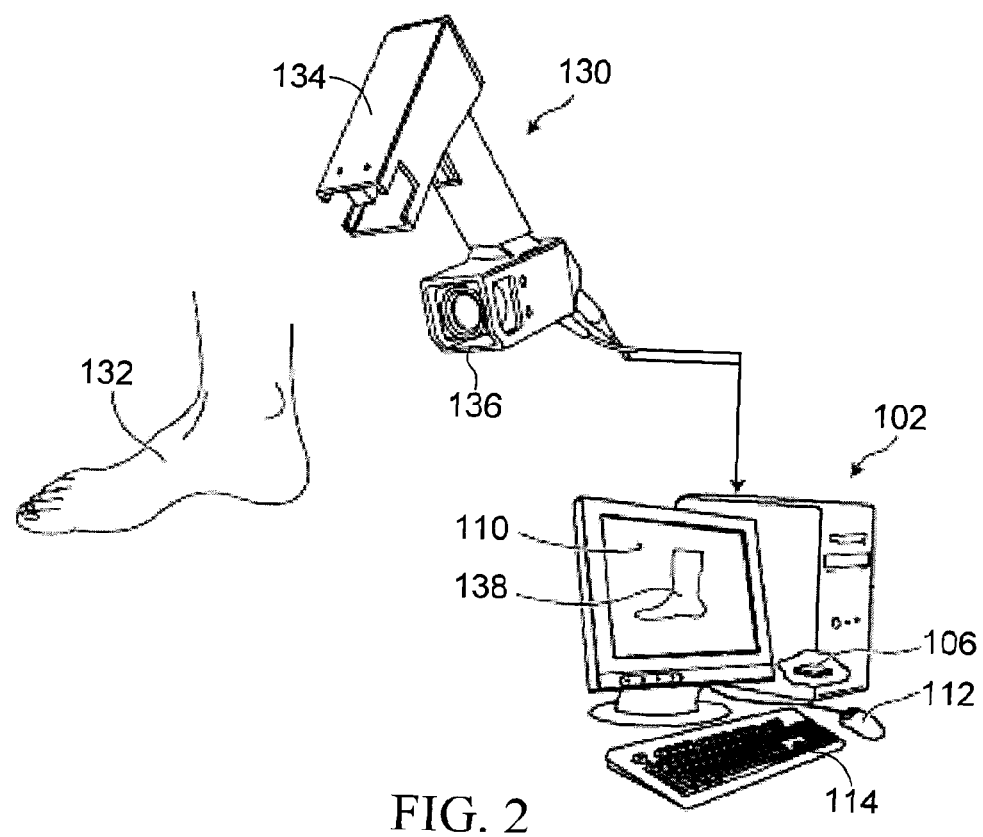
FIG. 2 is a perspective view of a scanner for receiving a signal encoded with the input plurality of coordinates representing a general shape of a part of a living body for use in the CAD/CAM system shown in FIG. 1.

Referring to FIG. 2, in one embodiment the CAD apparatus 102 is in communication with a scanner 130 for receiving a signal encoded with the input plurality of coordinates representing the general shape of a part of a living body, such as the foot 132 shown in FIG. 2. The scanned body part may be any body part, or group of body parts in any particular orientation, for which it is desired to produce an appliance. For example, the body part in the embodiment shown in FIG. 1 is a posterior region of a human patient's torso and legs and the scanned input coordinates are used to produce a supporting seat appliance for supporting the patient's body in a seated position.

In general the scanner 130 includes a structured light generator 134 for generating an illumination line, which illuminates the body part 132. The scanner 130 also includes a sensor 136 which is calibrated to produce an image of the intersection of the illumination line with the body part 132. The image is then processed by the scanner to extract a plurality of 3D input coordinates representing the body part 132. Examples of suitable scanners include the FastSCAN Cobra handheld scanner manufactured by Polhemus of Colchester, Vt., the Yeti Foot Scanner manufactured by Vorum Research Corporation of British Columbia, Canada, and the STARscanner™ manufactured by Orthomerica Products Inc. of California.

In one embodiment the appliance 120 is custom produced for a particular patient and the patient's body part, such as the foot 132, is scanned using the scanner 130. The input plurality of coordinates thus represent an actual shape of the patient's foot and are received at the apparatus 102 and displayed as a representation at 138 on the display 110. The operator may then use the pointing device 112 and the keyboard 114 to manipulate the representation 138 to provide a comfortably fitting appliance for the specific patient. Once the operator is satisfied with the appliance the modified appliance representation is output to the CAM machine 104 for machining of the final appliance.

Alternatively, a plurality of different body parts may be pre-scanned and stored in a library in the CAM apparatus 102.

Figure 3:
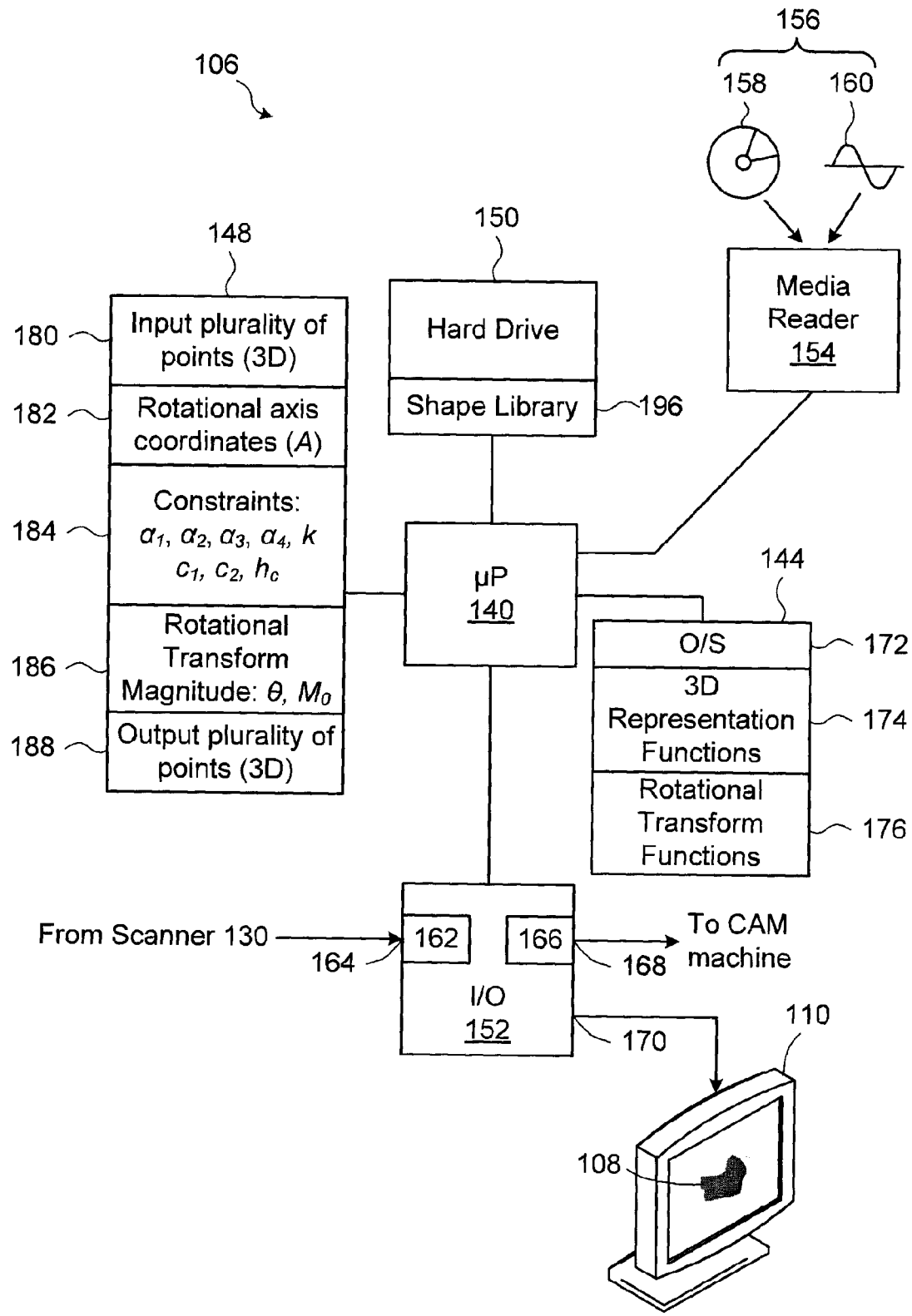
FIG. 3 is a processor circuit for implementing the CAD system shown in FIG. 1.

The library may thus include representations of various body parts or various sizes and may be used to provide an input plurality of coordinates for the CAM apparatus 102, which are then modified to suit a particular patient's requirements.
Processor Circuit The processor circuit 106 of the CAD apparatus 102 is shown in greater detail in FIG. 3. Referring to FIG. 3, the processor circuit 106 includes a microprocessor 140, a program memory 144, a random access memory (RAM) 148, a hard-drive 150, an input/output port 152, and a media reader 154, all of which are in communication with the microprocessor 140.

Program codes for directing the microprocessor 140 to carry out various CAD functions are stored in the program memory 144, which may be implemented as a random access memory (RAM), and/or a hard disc drive (HDD), or a combination thereof. The program memory 144 includes a block of codes 172 for directing the microprocessor 140 to provide general operating system (O/S) functions, and a 3D representation block of codes 174 for directing the microprocessor 140 to provide functions for producing the computer representation of the three-dimensional surface of the appliance. The program memory 144 further includes a rotational transform function block of codes 176 for directing the microprocessor to apply a rotational transform to a portion of the three-dimensional representation of the appliance.

The media reader 154 facilitates loading program codes into the program memory 144 from a computer readable medium 156 such as a CD ROM disc 158, a flash memory (not shown), or a computer readable signal 160 such as would be received over a network such as the internet, for example. In one embodiment the media reader may also facilitate writing carving instructions to a CD ROM disk computer readable medium 156 for a manual transfer between the CAD apparatus 102 and the CAM machine 104.

The RAM 148 includes a plurality of storage locations, including a store 180 for storing the input plurality of coordinates representing the appliance, a store 182 for storing rotational axis coordinates, a store 184 for storing constraints and blending parameters, a store 186 for storing a rotational transform magnitude, and a store 188 for storing an output plurality of coordinates.

The hard-drive 150 includes a plurality of storage locations for persistent storage of data, including a location 196 for storage of library shape data representing pre-scanned body parts.

The I/O 152 includes a first interface 162 having an input 164 for receiving signals encoded with the input plurality coordinates from the scanner 130 (shown in FIG. 2). The I/O 152 also includes a second interface 166 having an output 168 for producing the signal encoded with shape representation data or carving instructions for controlling the CAM machine 104 to produce the appliance. The interfaces 162 and 166 may be universal serial bus (USB) or RS232 serial interfaces, for example. The I/O 152 further includes an output 170 for producing display signals for causing the representation 108 of the appliance to be displayed on the display 110.
Operation Referring to FIG. 4, a flowchart depicting blocks of code for directing the processor circuit 106 to apply the rotational transform to a portion of the three-dimensional representation of the appliance is shown generally at 200. The blocks generally represent codes that may be read from the computer readable medium 156, and stored in the program memory 144, for directing the microprocessor 140 to perform various functions related to applying the rotational transform. The actual code to implement each block may be written in any suitable program language, such as C, C++, and/or assembly code for example.
Input Coordinates The process 200 begins at block 202 which directs the microprocessor 140 to receive an input plurality of coordinates representing a preliminary general shape of the appliance to be produced. In one embodiment, the input plurality of coordinates are read from the shape library 196 stored on the hard-drive 150, and are written to the store 180 of the RAM 148 to facilitate modification of the library shape for producing a custom appliance for a patient.

Figure 5:
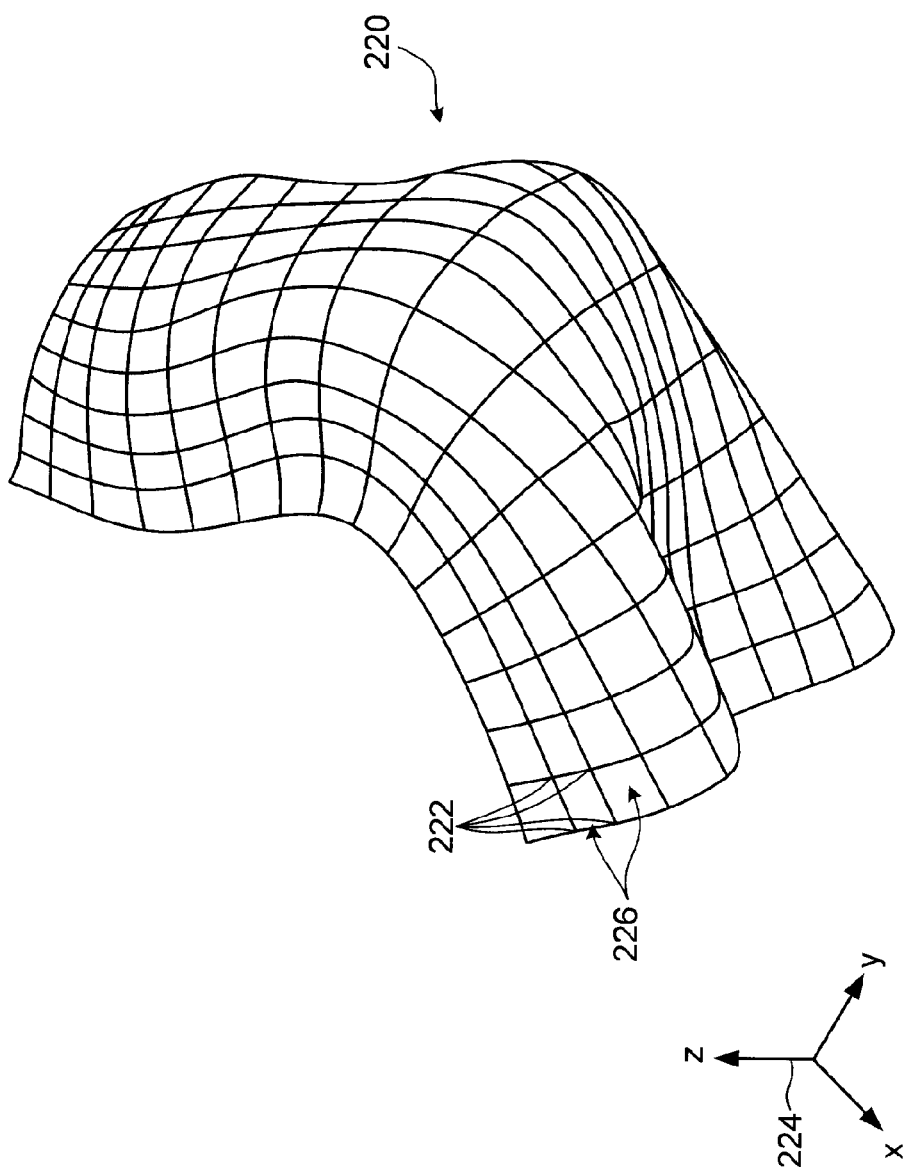
FIG. 5 is an exemplary 3D representation displayed by the processor circuit shown in FIG. 3.

The 3D representation 108, such as would be displayed on the display 110 is shown in greater detail in FIG. 5 at 220. Referring to FIG. 5, the input plurality of coordinates represent locations of vertices 222 within a Cartesian coordinate system 224 having x, y, and z axes. The vertex locations 222 define a plurality of polygons 226 forming an interconnected surface polygon mesh defining a general shape of the appliance. Such a surface polygon mesh may be efficiently stored in store 180 or the RAM 148 as a list of vertex locations 222, each having an associated list of connections to other vertices.

Figure 6:
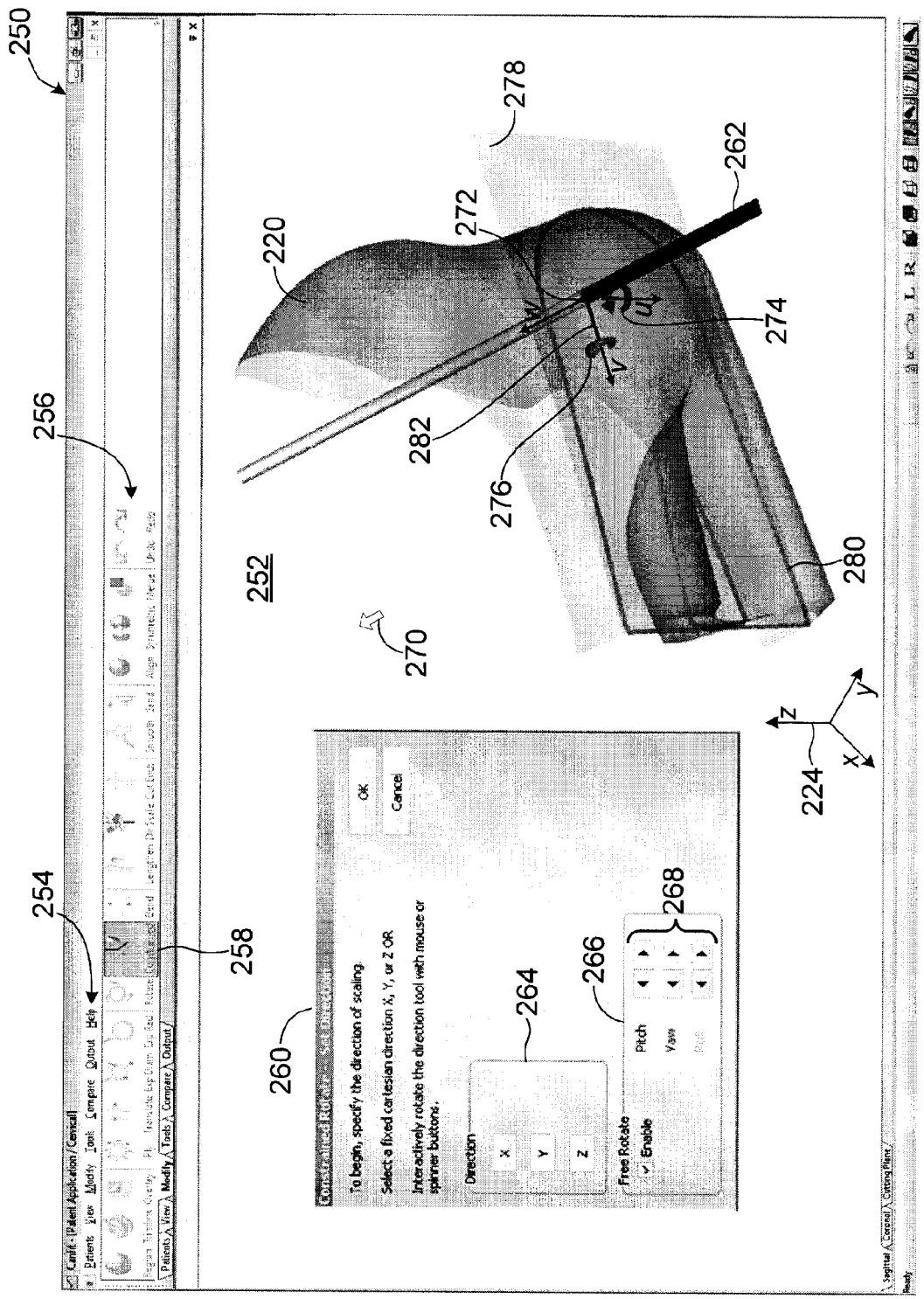
FIG. 6 is a screenshot of an operator interface for receiving input identifying a desired coordinate location of a rotational axis.

Referring to FIG. 6, a screenshot of an operator interface screen for displaying the preliminary 3D representation 220 and for facilitating modification of the 3D representation is shown generally at 250. The operator interface 250 includes a window 252 for displaying a view of the preliminary 3D shape representation 220. The operator interface 250 also includes a menu bar 254 for activating functions associated with receiving the input coordinates and displaying the representation 220. The operator interface 250 also includes a toolbar 256, including a plurality of actuator buttons providing for convenient invocation of some functions. For example, various CAD functions may be invoked to scale, move or rotate the 3D representation 220 within the window 252 to permit the operator to view various alternative views of the representation. In particular the toolbar 256 includes a "constrained rotation" button 258 for invoking the rotational transform function codes 176 (shown in FIG. 3).

In the embodiment shown, the representation 220 is displayed as a shaded appliance representation, where the polygons 226 have been shaded using a shading algorithm to display smooth surfaces in place of the polygon mesh shown in FIG. 5. In one embodiment a Gouraud shading algorithm is applied to the underlying polygons 226 to generate the displayed surface, as shown in FIG. 6.
Rotational Axis When the "constrained rotation" button 258 is selected by the operator using the pointing device 112, the process 200 (shown in FIG. 4) continues at block 204, which directs the microprocessor 140 to receive operator input identifying a coordinate location of a rotational axis about which the rotational transform is to be applied. In one embodiment, an operator interface window 260 is displayed, which facilitates receiving operator input identifying a desired coordinate location of a rotational axis. The rotational axis is represented in the window 252 by a 3D line 262 located at an initial or default location in the xyz coordinate system 224. The operator interface window 260 includes direction input controls 264 allowing the operator to enter directional coordinates x, y, and z defining a direction of the rotational axis 262. The operator interface window 260 further includes a control 266, that when enabled, permits free rotation of the rotational axis 262 such that the operator can select an axis direction by clicking on the pitch, roll, and yaw controls 268 to change the direction of the axis. Alternatively, the operator may interactively modify the direction of the rotational axis 262 about a point 272 by clicking and dragging on handles 274 and 276 associated with the rotational axis. The location of the point 272 with respect to the representation 220 may also be changed by using the pointing device 112 to drag the rotational axis 262 to a new location while the axis direction remains unchanged.

In the embodiment shown in FIG. 6, the representation of the rotational axis also includes a reference plane 278 intersecting the rotational axis 262 at the point 272. The reference plane 278 is oriented orthogonal to the rotational axis 262 and intersects the 3D representation 220 along an intersection line 280. The rotational axis 262 defines a coordinate system 282 for applying the rotational transform to the 3D representation 220. The coordinate system 282 has an origin at the point 272 on the reference plane 278, a w-axis aligned with the rotational axis 262, and u and v-axes lying in the reference plane 278.

In one embodiment the location of the rotational axis 262 may be stored as a 3D modeling matrix A defining the location of the uvw coordinate system 282 with respect to the xyz coordinate system 224:

$$A = \begin{bmatrix} a_{11} & a_{12} & a_{13} & 0 \\ a_{21} & a_{22} & a_{23} & 0 \\ a_{31} & a_{32} & a_{33} & 0 \\ a_{41} & a_{42} & a_{43} & 1 \end{bmatrix}, \quad \text{Eqn 1}$$

where the elements $a_{11}$, $a_{12}$, and $a_{13}$ represent a unit vector defining the u-axis of the coordinate frame, $a_{21}$, $a_{22}$, and $a_{23}$ represent a unit vector defining the v-axis of the coordinate frame, and $a_{31}$, $a_{32}$, and $a_{33}$ represent a unit vector defining the w-axis of the coordinate frame (i.e. the direction of the rotational axis 262). The elements $a_{41}$, $a_{42}$, and $a_{43}$ represent x, y, and z coordinates of the point 272 in the xyz coordinate system.

Referring back to FIG. 4, block 204 of the process 200 then directs the microprocessor 140 to store the coordinate location of the rotational axis 262 (i.e. the elements of the 3D modeling matrix A) in the rotational axis coordinate store 182 of the RAM 148.

Operator Input of Constraints

The process 200 then continues at block 206, which directs the microprocessor 140 to receive operator input of at least one constraint defining an extent of a transform volume within which the rotational transform is to be applied to the representation of the appliance 220.

Figure 7:
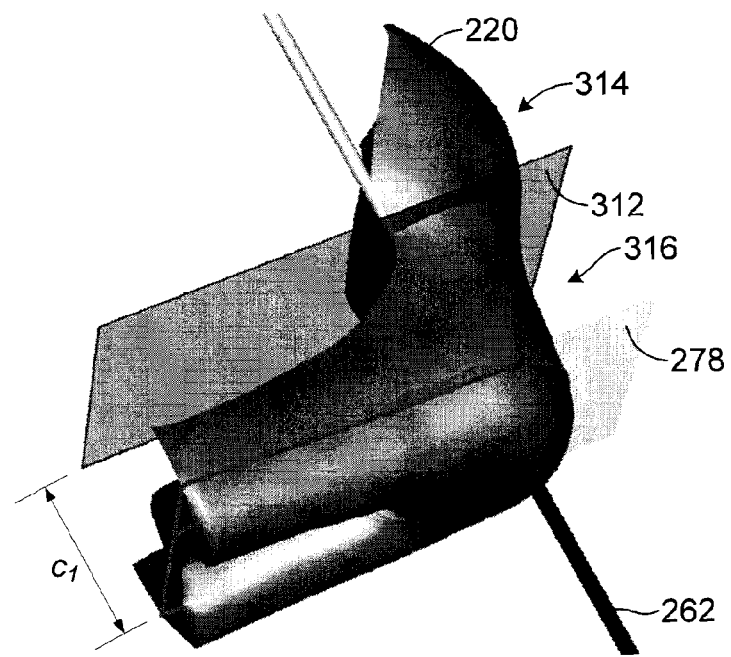
FIG. 7 is a perspective view of a 3D representation of an appliance.

Referring to FIG. 7, in one embodiment the at least one constraint comprises an axial constraint limiting an extent of the transform volume in a direction along the rotational axis 262. The axial constraint is represented by an axial constraint plane 312 oriented orthogonal to the rotational axis 262. In the embodiment shown the transform volume extends downwardly from the axial constraint plane 312 defining a portion 316 of the representation 220 to be modified by the rotational transform. The axial constraint plane 312 also defines a portion 314 of the 3D representation 220 (located above the axial constraint plane 312) that should remain un-modified after application of the rotational transform.

Figure 8:
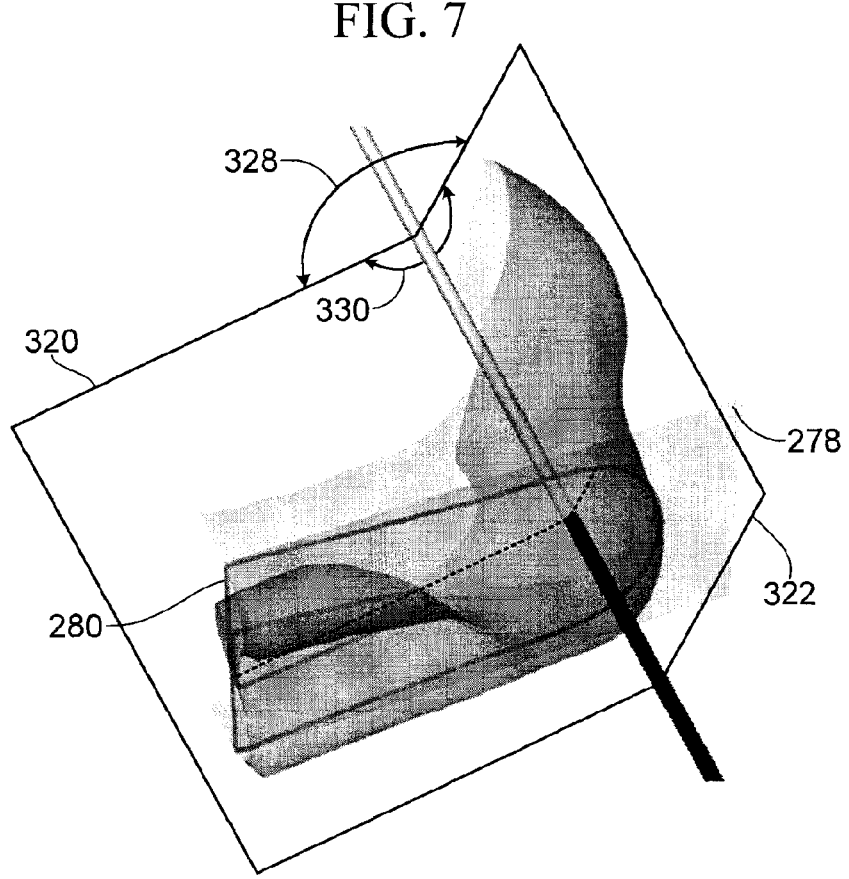
FIG. 8 is a further perspective view of a 3D representation of an appliance.

Referring to FIG. 8, in another embodiment the at least one constraint comprises first and second rotational constraints 320 and 322, which are represented by respective rotational constraint planes extending outwardly from the rotational axis 262. Together the first and second rotational constraints 320 and 322 define the transform volume within which the rotational transform is to be applied to the 3D representation 220. The first and second rotational constraints 320 and 322 limit an extent of the transform volume to a volume extending outwardly from the rotational axis and being bounded by the first and second rotational constraint planes. Portions of the 3D representation 220 located within a circular sector 328 between the first and second rotational constraints 320 and 322 are to be modified by the rotational transform, while other portions within a circular sector 330 are to remain un-modified by the rotational transform.

Alternatively, in some embodiments the transform volume may be bounded by both rotational constraints, such as the first and second rotational constraints 320 and 322 shown in FIG. 8, and one or more axial constraints, such as the axial constraint plane 312 (shown in FIG. 7).

Figure 9:
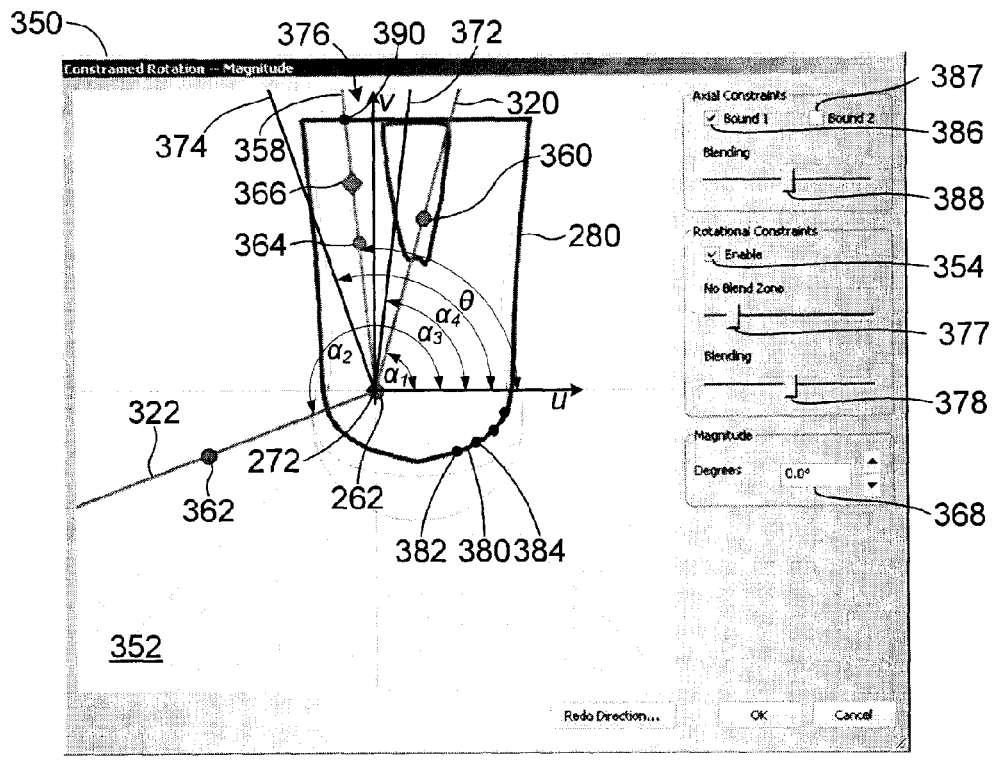
FIGS. 9 and 10 are screenshots of an operator interface for receiving operator input of rotational and/or axial constraints.

Referring to FIG. 9, a screenshot of the operator interface for receiving input of rotational and/or axial constraints is shown at 350. The operator interface 350 includes a window 352 for displaying a two-dimensional (2D) view of the intersection line 280 with respect to the u and v-axes of the coordinate system 282. In FIG. 9, the w-axis of the coordinate system 282 and the rotational axis 262 (shown in FIG. 6) are both located at the origin at point 272.

The line of intersection 280 is generated by determining which of the polygons 226 (shown in FIG. 5) intersect the reference plane 278 by computing a distance between each vertex 222 of each polygon, and determining whether the vertices all lie on the same side of the reference plane. Methods for computing a signed distance between an arbitrary point and a plane are well known in the art. A polygon that has at least one vertex 222 located on an opposite side of the reference plane to the remaining polygon vertices, intersects with the reference plane 278. The intersection of this polygon with the reference plane defines a line segment, such as the exemplary line segment 380 shown in FIG. 9. The line segment 380 has a pair of endpoints 382 and 384, each of which lie on one of the edges of the intersecting polygon defined by adjacent vertices. The computed distances between the vertices and the reference plane may then be used to interpolate between the coordinates of the adjacent vertices to obtain the coordinate locations of the endpoints. The line of intersection 280 is thus made up of a plurality of line segments, such as the line segment 380.

The operator interface 350 includes a checkbox field 354, which when activated by clicking on the checkbox causes the first and second rotational constraints 320 and 322 to be activated and displayed. The first and second rotational constraints 320 and 322 appear in the window 352 as respective rotational constraint lines extending outwardly from the rotational axis 262. The rotational constraints 320 and 322 each have respective controls 360 and 362 that facilitate interactive positioning of the rotational constraints with respect to the intersection line 280 when the controls are clicked and dragged using the pointing device 112. The first rotational constraint 320 is oriented at an angle $a_1$ to the u-axis and the second rotational constraint 322 is oriented at an angle $a_2$ to the u-axis. In the embodiment shown in FIG. 9, the intersection line 280 represents a cross section through the seat appliance 220 and the second rotational constraint 322 is oriented such that a right leg portion and a posterior region of the seat appliance 220 will remain unmodified by the rotational transform.

Figure 10:
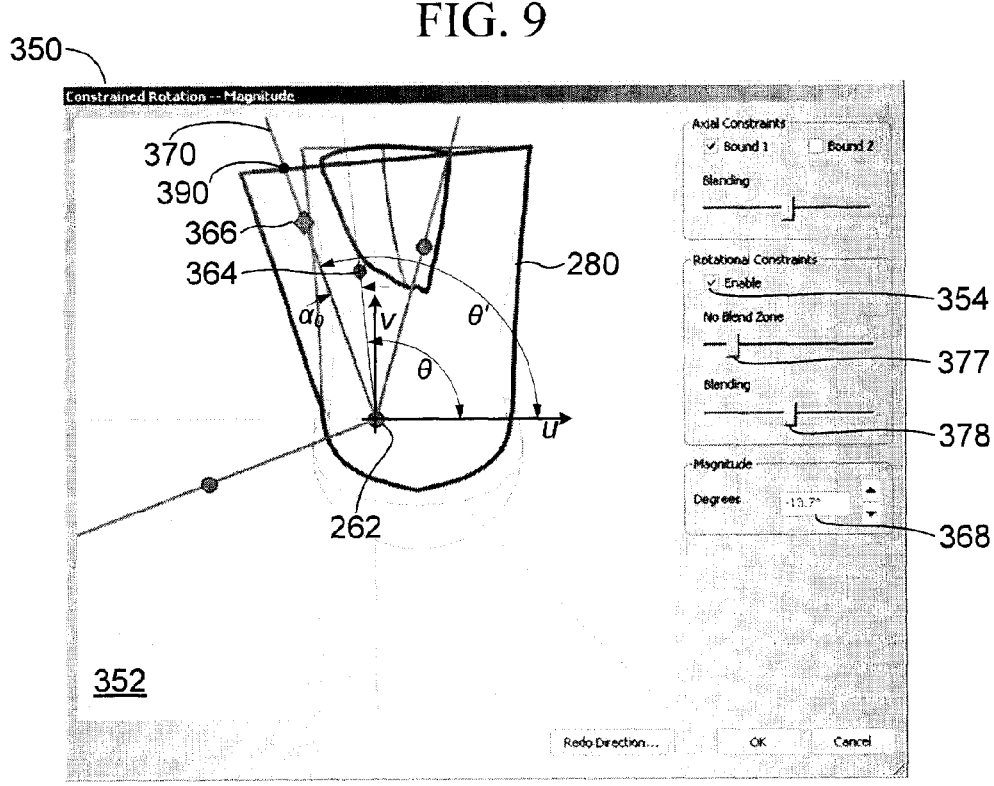

In embodiments such as that shown in FIG. 9 and FIG. 10, where rotational constraints are activated, only a portion of the 3D representation lying within the transform volume is subjected to the rotational transform. To avoid producing shape discontinuity at the edges of the transform volume, rotational blending may be applied in the region of the rotational constraints to cause continuity of shape between modified portions of the representation and un-modified portions of the representation following application of the rotational transform.

In the embodiment shown, the operator interface 350 includes a slider control 378 which facilitates receiving operator input of a blending parameter k that controls application of the rotational blending, as described later herein. The operator interface 350 further includes a slider control 377 which facilitates receiving operator input of a desired size of the no-blending zone 376. The no-blending zone 376 extends between a line 372 at an angle $a_3$ to the u-axis and a line 374 at an angle $a_4$ to the u-axis and is centered on the reference line 358. The lines 372 and 374 also define respective rotational blending regions extending between the rotational constraint 320 and the line 372, and the line 374 and the second rotational constraint 322. In general, a full magnitude of the rotational transform is applied in the no-blending zone 376, while in the rotational blending zones the applied magnitude of the rotational transform is reduced in proximity to the rotational constraints 320 and 322. The effect of the rotational blending regions and the no-blending zone 376 is described in greater detail later herein.

The operator interface 350 also includes a checkbox field 386, which when activated by clicking on the checkbox causes a first axial constraint to be activated (such as the axial constraint 312 shown in FIG. 7). The operator interface 350 also includes a checkbox field 387, which when activated by clicking on the checkbox causes a second axial constraint to be activated. In the embodiment shown, only the first axial constraint is activated. When an axial constraint is activated, a constraint plane such as the plane 312 shown in FIG. 7 is displayed, and may be dragged to a location along the rotational axis 262 in response to operator input. In the example shown, the axial constraint plane 312 is located a distance $c_1$ along the rotational axis 262 from the reference plane 278. The axial constraint plane 312 is thus located at $w=c_1$. Similarly, if a second constraint is activated by the operator clicking the checkbox field 387, a second constraint plane would be located at a location $w=c_2$.

The operator interface 350 further includes a slider control 388, which facilitates receiving operator input of size $h_c$ of an axial blending region, which is stored in the constraints store 184 of the RAM 148. When an axial constraint is activated, the axial blending region extends from the axial constraints into the transform volume. In general the axial blending is operable to cause continuity of shape between modified portions of the representation of the appliance within the transform volume and un-modified portions of the representation of the appliance outside the transform volume. The application of axial blending within the axial blending regions is described later herein.

Referring back to FIG. 4, block 206 of the process 200 then directs the microprocessor 140 to store the values of the constraints $a_1$ and $a_2$, the no-blending zone angles $\alpha_3$ and $\alpha_4$, and the blending parameter k in the constraints store 184 of the RAM 148 (shown in FIG. 3). Block 206 also directs the microprocessor 140 to store the values of the constraint plane locations $c_1$ and $c_2$ in the constraints store 184 of the RAM 148.

Operator Input of Rotational Transform Magnitude

The process 200 then continues at block 208 which directs the microprocessor 140 to receive operator input of a magnitude of the rotational transform to be applied to the portion of the representation of the appliance within the transform volume. Referring again to FIG. 9, in this embodiment the magnitude of the rotational transform to be applied is defined with respect to a reference line 358 displayed in the window 352. The reference line 358 extends outwardly from the rotational axis 262 and is located at a reference angle θ from the u-axis. The reference line 358 includes a first control 364 for setting a reference angle θ for the rotational transform, which allows the operator to align the reference line with a particular feature of the appliance (in this case the reference line 358 is generally centered on the left limb portion).

The operator interface 350 also includes a second control 366 for setting the rotational transform magnitude $M_0$ with respect to the reference line 358. The operator interface 350 further includes a magnitude field 368, which is linked to the second control 366 for displaying and/or receiving operator input of the rotational transform magnitude $M_0$. Initially as shown in FIG. 9, the second control 366 lies on the reference line 358 and the magnitude field 368 displays a value of $M_0=0.0°$ (i.e. zero magnitude). As shown in FIG. 10, when a non-zero angular magnitude value is entered into the magnitude field 368 ($M_0=-13.7°$ in this case), the second control 366 moves to a new location along with the line 370. The line 370 is angularly displaced from the reference line 358 by the entered value of the angular magnitude $M_0$. In this embodiment a sign convention is implemented such that anti-clockwise displacements are given a negative sign, while clockwise displacements are given a positive sign. Alternatively, the operator may also drag the second control 366 to a desired new location, causing the line 370 to be displayed as shown while the magnitude field 368 is updated to reflect the angular location of the line 370 with respect to the reference line 358. The control 364 and the reference line 358 remain located at the zero magnitude reference angle θ.

Referring back to FIG. 4, block 208 of the process 200 then directs the microprocessor 140 to store the values of the reference angle $\alpha_3$ and the magnitude $M_0$ (in this case $M_0=-13.7°$) in the rotational transform magnitude store 186 of the RAM 148 shown in FIG. 3.

Figure 4:
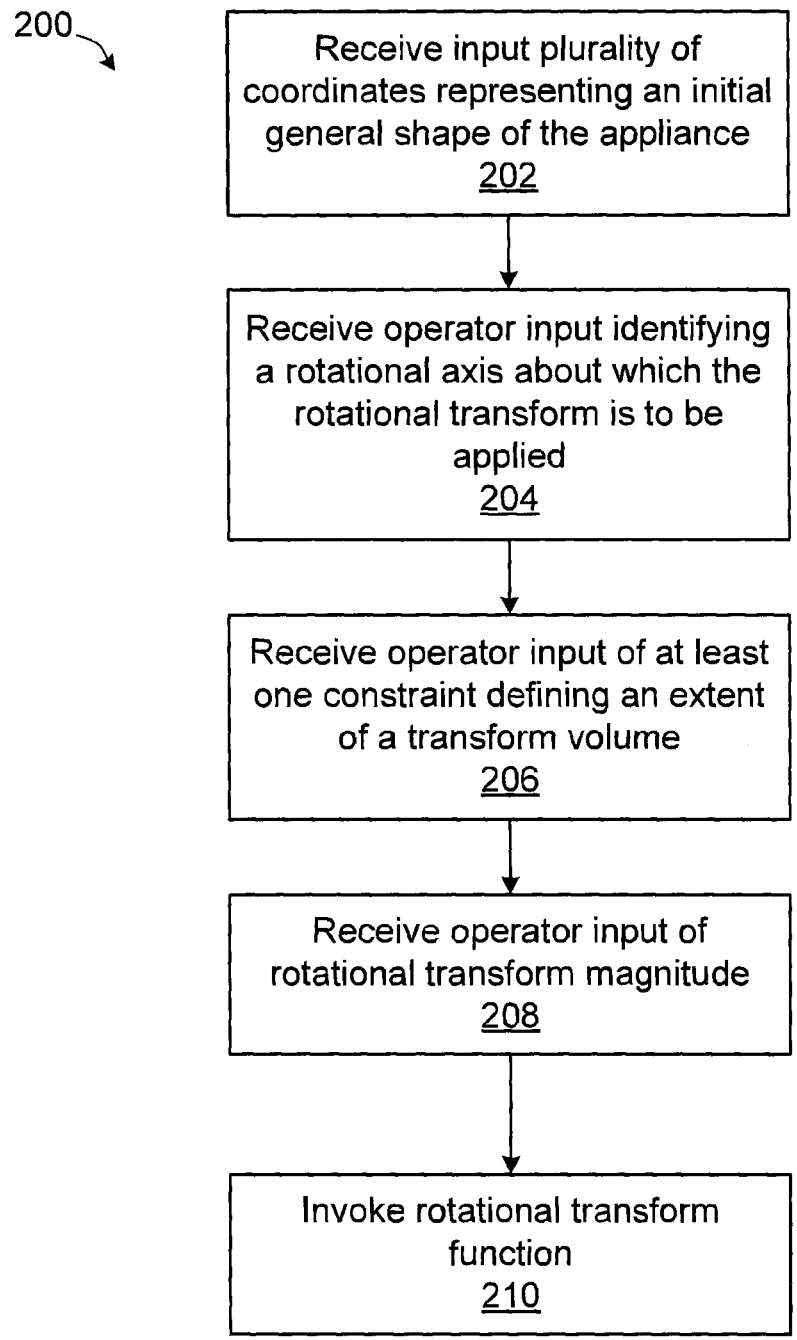
FIG. 4 is a flowchart of blocks of code for directing the processor circuit shown in FIG. 3 to apply a rotational transform to a portion of a three-dimensional representation of an appliance.
Figure 11:
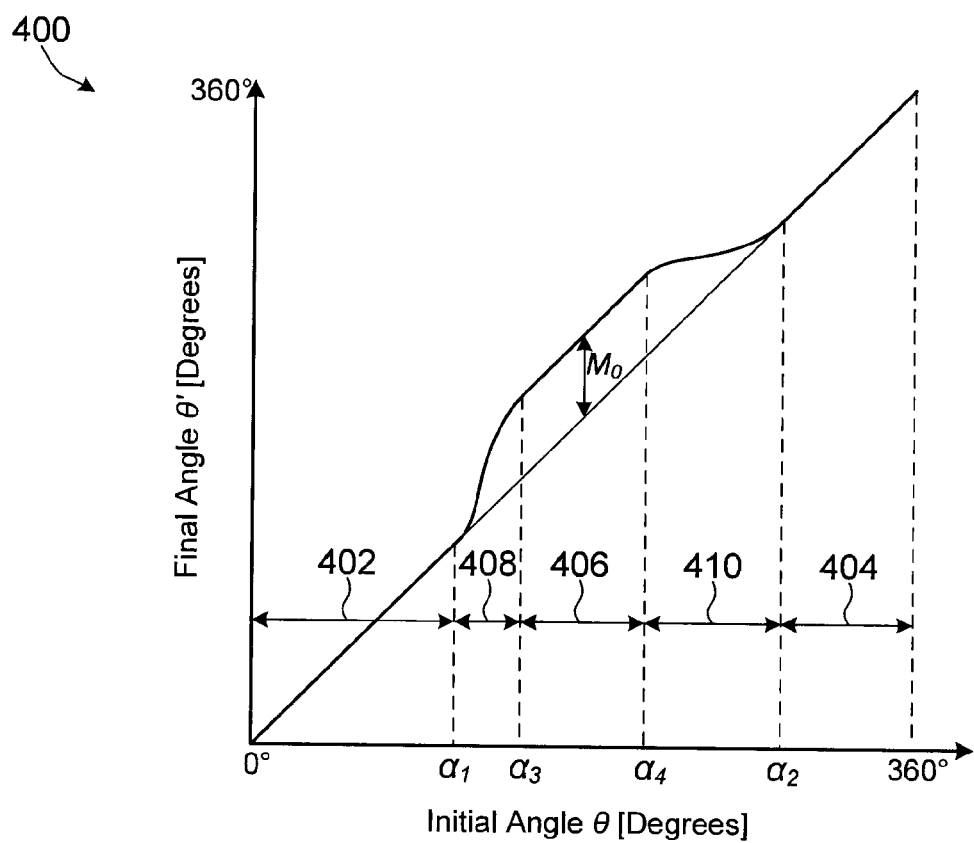
FIG. 11 is a graphical depiction of an angular mapping between initial angle and final angle.

Following execution of the codes represented by block 208 in FIG. 4, all necessary parameters are available for computing a rotational magnitude that should be applied to each of the input plurality of coordinates within the transform volume. Referring to FIG. 11, a graphical depiction of an angular mapping between initial angle and final angle is shown generally at 400. The graph 400 maps an initial angle θ for any point on the intersection line 280 (for example the point 390 shown in FIG. 9) to a final angle θ' for the point (shown in FIG. 10). Points lying in a region 402 and in a region 404 are mapped 1:1 and thus remain un-modified i.e. for $0° \leq \theta \leq \alpha_1$ and for $\alpha_2 \leq \theta \leq 360°$:

$$M(\theta)=0. \qquad \text{Eqn 2}$$

Points lying in an expansion region 408 are rotated by progressively increasing angular displacements up to the full magnitude $M_0$ to provide continuity with the region 402 at the second rotational constraint. For the region 408, i.e. for $\alpha_1 \leq \theta \leq \alpha_3$, define $$w = \frac{\theta - \alpha_1}{\alpha_3 - \alpha_1},$$

then
for $0 \leq W \leq 0.5$:

$$M(\theta) = \frac{M_0}{2}(2w)^k,$$

for $0.5 < w \leq 1$:

$$M(\theta) = \frac{M_0}{2}(2 - (2-2w)^k).\qquad\text{Eqn 3}$$

The above blending functions yield $M(\theta)=0$ when $w=0$, $M(\theta)=M_0/2$ when $w=0.5$, and $M(\theta)=M_0$ when $w=1$. The maximum slope of the blending function occurs at $w=0.5$ and the parameter k, which usually ranges between 1 and 4, determines the steepness of the slope and thus the shape of the blending in the expansion region 408.

Points lying in the no-blending region 406 are rotated by the full rotational transform magnitude $M_0$, i.e. for $\alpha_3 \leq \theta \leq \alpha_4$:

$$M(\theta) = M_0 \qquad\text{Eqn 4}$$

Points lying in a compression region 410 are rotated by progressively reducing angular displacements to provide continuity with the region 404 at the first rotational constraint i.e. for $\alpha_4 \leq \theta \leq \alpha_2$, define $$w = \frac{\theta - \alpha_4}{\alpha_2 - \alpha_4},$$

then
for $0 < w \leq 0.5$:

$$M(\theta) = \frac{M_0}{2}(2 - (2-2w)^k),$$

and
for $0.5 < w \leq 1$:

$$M(\theta) = \frac{M_0}{2}(2w)^k \qquad\text{Eqn 5}$$

The equations 2-5 provided above may be used to calculate the rotational transform magnitude that should be applied performing the rotational transform. Alternatively, the graph 400 shown in FIG. 11 may be saved as a look-up table mapping initial angle $\theta$ to final angle $\theta'$.

Applying the Rotational Transform

Still referring to FIG. 4, block 210 then directs the microprocessor 140 to invoke the rotational transform function 176 in the program memory 144.

Figure 12:
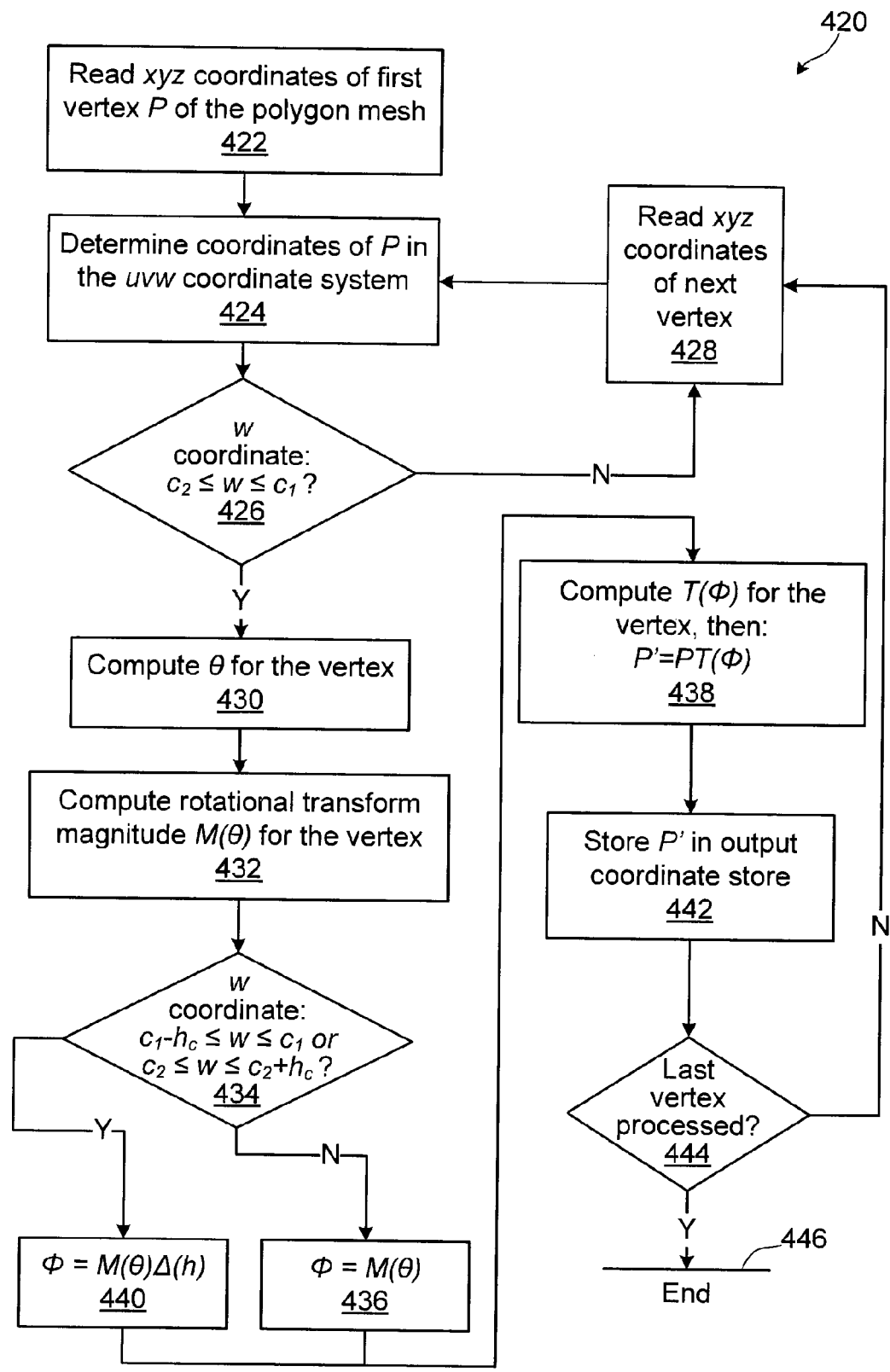
FIG. 12 is a flowchart of blocks of code for directing the processor circuit shown in FIG. 3 to apply a rotational transform to the portion of the 3D appliance representation.

Referring to FIG. 12, a flowchart depicting blocks of code for directing the microprocessor 140 to apply the rotational transform to the portion of the 3D appliance representation within the transform volume is shown generally at 420. The process begins at block 422, which directs the microprocessor 140 to read the coordinates of a first vertex in the input plurality of coordinates from the store 180 of the RAM 148. Each vertex may be represented by a vector:

$$\overline{P} = [P_x P_y P_z 1].$$

Block 424 then directs the microprocessor 140 to determine coordinates of the vector $\overline{P}$ in the uvw coordinate system by reading the 3D modeling matrix A from the store 182 of the RAM 148 and computing the inverse of A. The uvw coordinates of the vector $\overline{P}$ are obtained as follows:

$$\overline{P}_{uvw} = \overline{P} A^{-1}.\qquad\text{Eqn 6}$$

Block 426 then directs the microprocessor 140 to determine whether the vertex lies within the axial constraint planes. If only one axial constraint plane is active, as shown in FIG. 7, any w-coordinate value that is less than $c_1$ identifies the vertex as lying within the axial constraints. When more than one constraint is active, the w-coordinate must have a value between $c_2$ and $c_1$ for the vertex to lie within the axial constraints. If at block 426 the w-coordinate lies outside the constraint planes, then the process continues at 428, which directs the microprocessor 140 to read the xyz coordinates of next vertex. Block 428 then directs the microprocessor 140 back to block 424.

If at block 426 the w-coordinate lies within the constraint planes, then the process continues at 430. Block 430 directs the microprocessor 140 to compute the angle $\theta$ within the uv plane for the vertex as follows:

$$\theta = \arctan\left(\frac{u}{v}\right).\qquad\text{Eqn 7}$$

The process then continues at block 432 which directs the microprocessor 140 to use Eqn's 2-5 to compute rotational transform magnitude $M(\theta)$ for the vertex, using the value of $\theta$ computed at block 430.

Block 434 then directs the microprocessor 140 to determine whether the vertex lies within the axial blending region defined by the axial blending parameter $h_c$. If the vertex lies outside the axial blending regions, then the process continues at block 436, which directs the microprocessor 140 to set the angular displacement $\Phi$ of the vertex to the value of $M(\theta)$ determined at block 432.

If at block 434 the vertex lies inside the axial blending regions, then the process continues at block 440, which directs the microprocessor 140 to determine the angular displacement $\Phi$ of the vertex by multiplying the value of $M(\theta)$ determined at block 432 by a blending function $\Delta(h_c)$. In one embodiment blending is applied in accordance with a cubic polynomial:

$$\Delta(h) = 3\left(\frac{h}{h_c}\right)^2 - 2\left(\frac{h}{h_c}\right)^3,\qquad\text{Eqn 8}$$

where h is a distance into the transform volume from the first or second constraint and $h_c$ is the size or extent of the axial blending region.

The process then continues at block 438 which directs the microprocessor 140 to compute a rotational transform matrix $T(\Phi)$ for applying the rotational displacement $\Phi$ computed at block 436 or 440 to the vector $\overline{P}$, in order determine coordinates of the rotated vertex in the xyz coordinate system. For rotation of the vector $\overline{P}$ through an angle $\Phi$ about the rotational axis 262 passing through a point Q taken as the point of intersection 272 between the reference plane 278 and the rotational axis 262, where:

$$Q = [Q_x, Q_y, Q_z],$$

and where the axis has a direction $\overline{U}$:

$$\overline{U} = [U_x, U_y, U_z],$$

the rotational transform matrix $T(\Phi)$ is given by:

$$T(\phi) = \begin{bmatrix} [T_{u,\phi}] & \begin{bmatrix}0\\0\\0\end{bmatrix} \\ [Q - QT_{u,\phi}] & [1] \end{bmatrix},\qquad\text{Eqn 9}$$

where $T_{u,\Phi}$ is a 3×3 sub-matrix:

$$T_{u,\Phi} = (\cos\phi)I + (1-\cos\phi)\overline{U}\otimes\overline{U} + (\sin\phi)\tilde{U},\quad \text{Eqn 10}$$

and where:

$$I = \begin{bmatrix} 1 & 0 & 0 \\ 0 & 1 & 0 \\ 0 & 0 & 1 \end{bmatrix},$$

a 3×3 unit matrix;

$$\tilde{U} = \begin{bmatrix} 0 & -U_z & U_y \\ U_z & 0 & -U_x \\ -U_y & U_x & 0 \end{bmatrix},$$

i.e. a skew symmetric matrix; and $$\overline{U}\otimes\overline{U} = \begin{bmatrix} U_xU_x & U_xU_y & U_xU_z \\ U_yU_x & U_yU_y & U_yU_z \\ U_zU_x & U_zU_y & U_zU_z \end{bmatrix},$$

the tensor product of U with itself.

The transformation matrix $T(\Phi)$ is computed for each vertex $\overline{P}$, and the modified 3D xyz coordinates of the vertex are determined by the following matrix multiplication:

$$\overline{P}' = \overline{P}T(\phi). \quad \text{Eqn 11}$$

Block 442 then directs the microprocessor 140 to store the modified xyz coordinates for the vertex in the P' in the store 188 of the RAM 148.

Block 444 then directs the microprocessor 140 to determine whether the last vertex has been processed. If further vertices remain to be processed then block 444 directs the microprocessor 140 to block 428, which directs the microprocessor to read xyz coordinates of the next vertex from the store 180 of the RAM 148. Block 428 then directs the microprocessor 140 back to block 424.

If at block 444, the last vertex has been processed then all vertices within the transform volume have been processed and the process 420 ends at 446. The output plurality of coordinates representing the final appliance may be displayed on the display 110, as shown in FIG. 6.

Example 1

Figure 13:
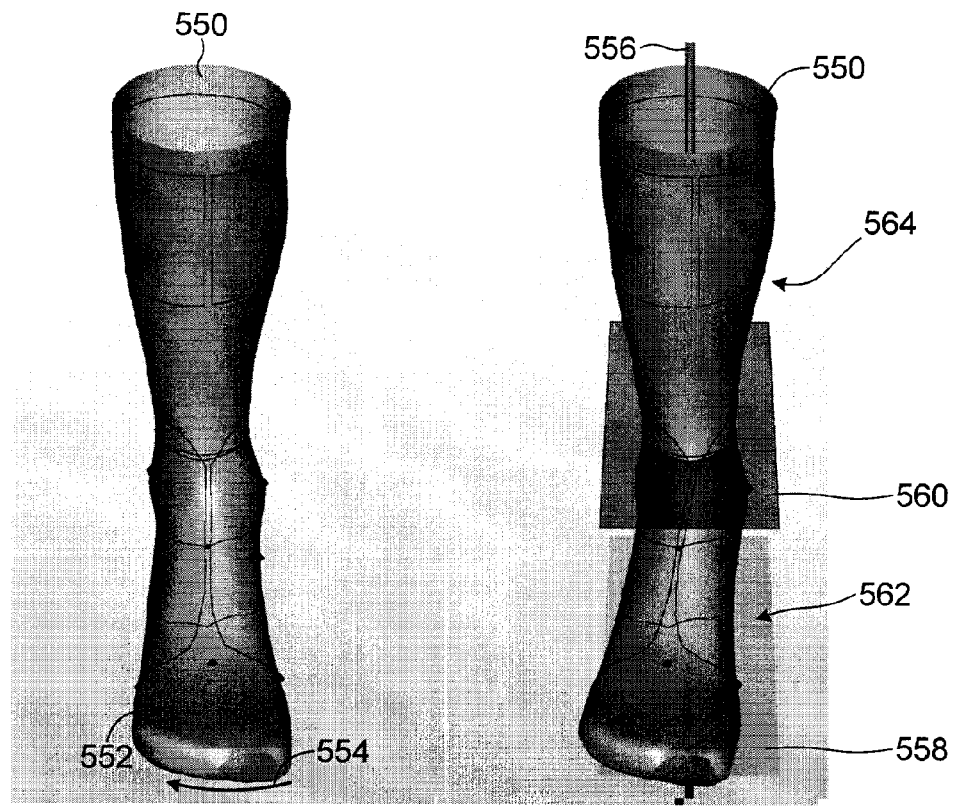
FIG. 13 is a screenshot of an appliance modification performed in accordance with a first example.

In one example, the process described above may be applied to modify a library shape of an ankle/foot orthotic appliance to turn the foot portion relative to the leg portion to accommodate for a patient's adduction (draw toward the midline of the body) or abduction (draw away from the midline of the body). Referring to FIG. 13, in an abduction example, it is desired to modify a library shape 550 to cause a foot portion 652 to be shifted outwardly in the direction shown by the arrow 554. In this embodiment, a rotational axis 556 is defined as described above in connection with FIG. 6, where the axis is oriented passing generally through an ankle portion (not shown) of the foot. A reference plane 558 is located passing through the foot and an axial constraint plane 560 is defined partway up the leg of the appliance 550. The axial constraint plane 560 defines a portion 562 of the appliance 550 that is to be modified by the rotational transform and a portion 564 of the appliance that is to remain un-modified.

Figure 14:
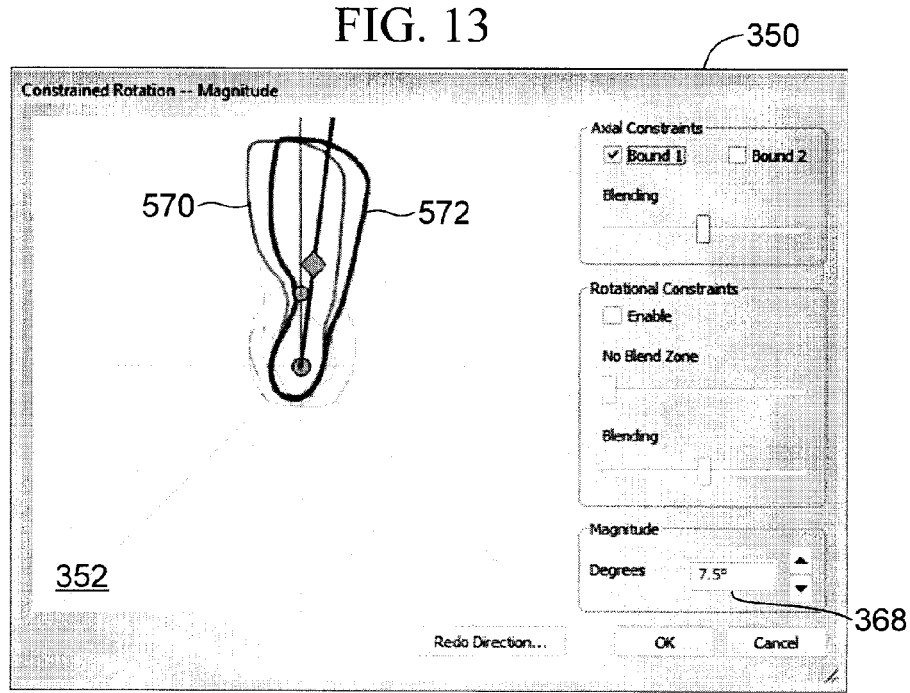
FIG. 14 is a screenshot of the operator interface shown in FIG. 9 for the appliance modification example shown in FIG. 13.

The operator interface 350 for this embodiment is shown in FIG. 14. Referring to FIG. 14, the window 352 of the operator interface 350 displays a 2D view of the intersection of the appliance with the reference plane, and in this case the operator has entered a rotational magnitude of 7.5° in the magnitude field 368. In this embodiment, the transform volume encompasses the entire foot portion below the axial constraint plane 560 and no rotational constraints are selected. Accordingly, there is no rotational blending to be accounted for when applying the rotational transform and a the full magnitude $M(\theta)=M_0=7.5°$ is applied to all vertices below the axial constraint plane 560. Since an axial constraint is active, blending is applied proximate to the axial constraint plane 560 as described above in accordance with the selected value of $h_c$. The window 352 displays an initial location 570 and a final location 572 of the portion of the foot lying in the reference plane.

Example 2

Figure 15:
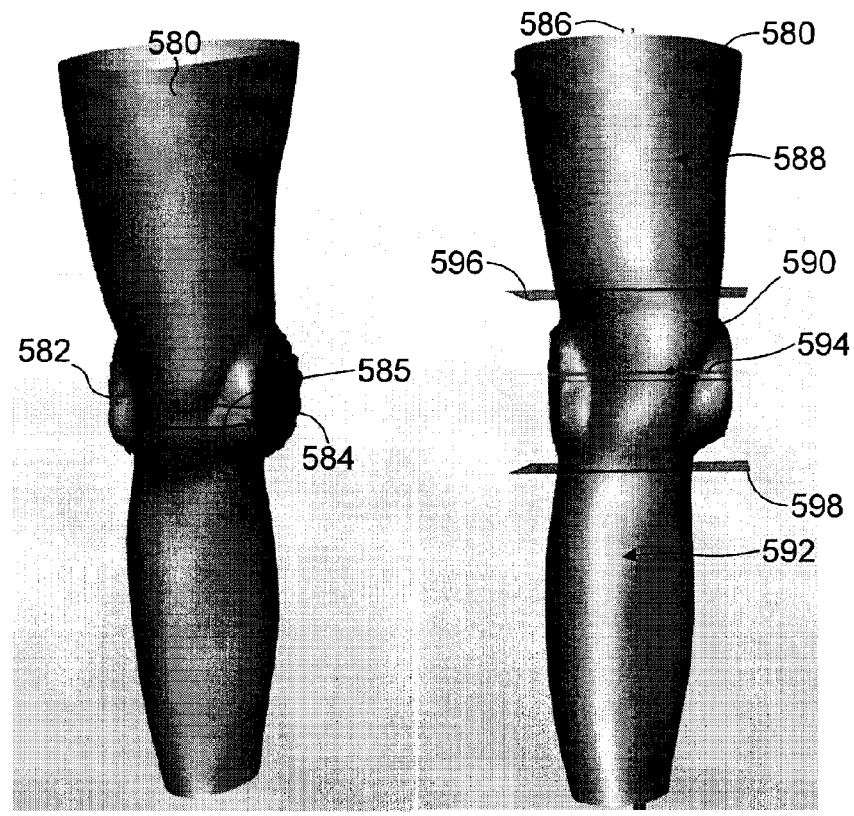
FIG. 15 is a screenshot of an appliance modification performed in accordance with a second example.

In another example, the process described above may be applied to modify a library shape of a knee brace by changing a hinge direction. Referring to FIG. 15, a library shape 580 of a knee brace is shown having hinge flats 582 and 584, and for which it is desired to rotate the hinge direction in the direction indicated by the arrow 585. A rotational axis 586 is defined as described above in connection with FIG. 6, where the axis is oriented passing generally through the center of an upper limb portion 588, knee portion 590, and lower limb portion 592. A reference plane 594 is located passing through the knee portion 590. A first axial constraint plane 596 is located above the knee portion 590 to prevent the upper limb portion 588 from being modified by the rotational transform. Similarly, a second axial constraint plane 598 is located below the knee portion 590 to prevent the lower limb portion 592 from being modified by the rotational transform.

Figure 16:
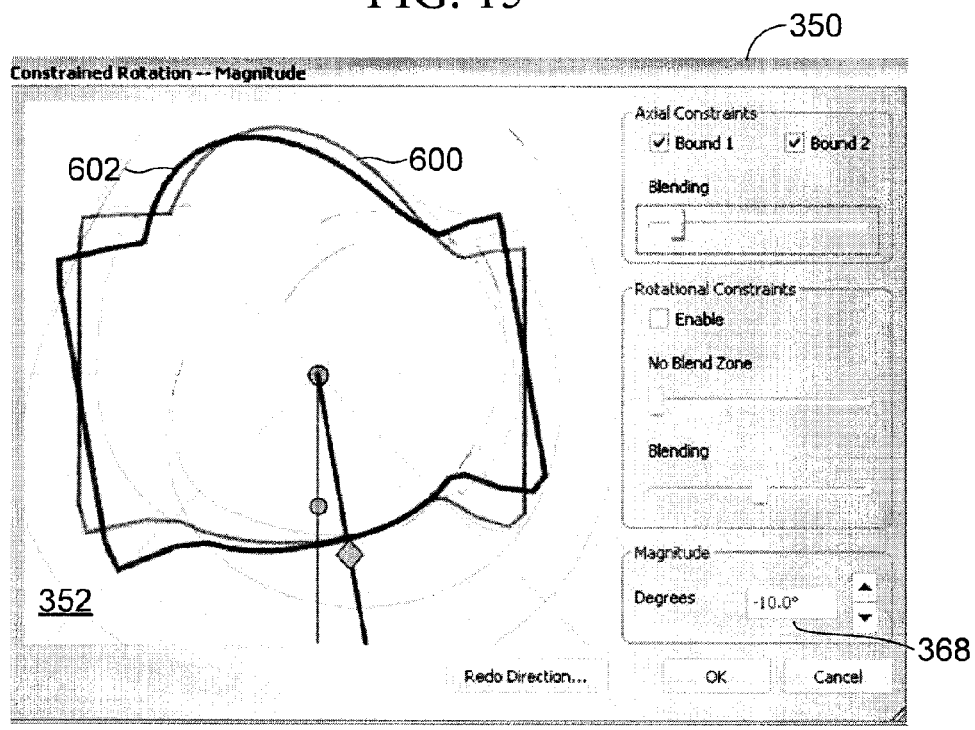
FIG. 16 is a screenshot of the operator interface shown in FIG. 9 for the appliance modification example shown in FIG. 15.

The operator interface 350 for this embodiment is shown in FIG. 16. Referring to FIG. 16, the window 352 of the operator interface 350 displays a 2D view of the intersection of the appliance with the reference plane, and in this case the operator has entered a rotational magnitude of −10° in the magnitude field 368. In this example, the entire knee portion is to be rotated and accordingly, no rotational constraints are selected and the full magnitude $M(\theta)=M_0=-10°$ is applied to all vertices between the first and second axial constraint planes 596 and 598. Blending is applied proximate to each of the axial constraint planes 596 and 598 to preserve continuity between the knee portion 590 and the upper and lower limb portions 588 and 592 respectively. The window 352 displays an initial location 600 and a final location 602 of the portion of the foot lying in the reference plane.

Advantageously, the process described herein facilitates rotation of a 3D shape, such that only a portion of the shape is altered by the 3D rotation. The process also permits the rotation to occur about an operator specified axis. Blending between modified and un-modified portions of the shape prevent discontinuities being introduced by the modifications.

While specific embodiments of the invention have been described and illustrated, such embodiments should be considered illustrative of the invention only and not as limiting the invention as construed in accordance with the accompanying claims.

What is claimed is:

1. A method for applying a rotational transform to a portion of a three-dimensional representation of an appliance for a living body, the representation being defined by an input plurality of coordinates stored in a processor circuit memory, the input plurality of coordinates representing a general shape of the appliance, the method comprising:

receiving operator input identifying a coordinate location of a rotational axis about which the rotational transform is to be applied;

receiving operator input of a constraint defining an extent of a transform volume within which the rotational transform is to be applied to the representation of the appliance, said constraint comprising first and second rotational constraints with respect to the rotational axis, said first and second rotational constraints defining an angular extent of said transform volume about said rotational axis;

receiving operator input of a rotational transform magnitude;

applying the rotational transform to the portion of the representation of the appliance within the transform volume to produce an output plurality of coordinates representing a modified shape of the appliance such that the general shape of portions of the appliance outside the transform volume remain un-modified by the rotational transform; and storing the output plurality of coordinates in the processor circuit memory.

2. The method of claim 1 further comprising generating a set of instructions operable to control a computer aided manufacturing machine to produce one of the appliance and a mold for producing the appliance in accordance with said output plurality of coordinates.

3. The method of claim 1 wherein receiving said operator input of said constraint comprises receiving operator input of at least one axial constraint limiting an extent of the transform volume in a direction along the rotational axis.

4. The method of claim 3 wherein receiving said operator input defining said at least one axial constraint comprises receiving operator input defining at least one constraint plane oriented orthogonal to the rotational axis and intersecting the appliance representation.

5. The method of claim 3 wherein receiving said operator input defining said at least one axial constraint comprises receiving operator input defining first and second spaced apart axial constraints along the rotational axis, the first and second axial constraints limiting an extent of the transform volume to between the first and second axial constraints.

6. The method of claim 3 further comprising:

identifying an axial blending region extending into said transform volume from said at least one axial constraint; and wherein applying the rotational transform comprises reducing a magnitude of the rotational transform within said axial blending region to cause continuity of shape between modified portions of the representation of the appliance within said transform volume and un-modified portions of the representation of the appliance outside said transform volume.

7. The method of claim 6 wherein reducing said magnitude of the rotational transform comprises applying a rotational transform having:

substantially zero magnitude at said axial constraint; and a magnitude that progressively increases with distance away from said at least one axial constraint to reach a full rotational transform magnitude beyond said axial blending region.

8. The method of claim 1 wherein applying the rotational transform to said portion of the three-dimensional representation of the appliance within said transform volume comprises:

identifying first and second rotational blending regions extending from said first and second rotational constraints into said transform volume; and wherein applying the rotational transform comprises reducing a magnitude of the rotational transform within said first and second rotational blending regions respectively to cause continuity of shape between modified portions of the representation of the appliance within said transform volume and un-modified portions of the representation of the appliance outside said transform volume.

9. The method of claim 8 wherein reducing said magnitude of the rotational transform comprises applying a rotational transform having:

substantially zero magnitude at said first and second rotational constraints; and a magnitude that progressively increases with rotational displacement into said transform volume to reach a full rotational transform magnitude beyond said first and second rotational blending regions respectively.

10. The method of claim 8 wherein identifying said first and second rotational blending regions comprises:

receiving operator input of a no-blending zone located between said first and second rotational constraints, said no-blending zone defining an angular extent of the transform volume about said rotational axis within which a full magnitude of the rotational transform is to be applied, and wherein said first and second rotational blending regions respectively comprise portions of the transform volume outside said no-blending zone.

11. The method of claim 1 further comprising receiving operator input of a desired rotational magnitude and direction of the rotational transform to be applied to said portion of the three-dimensional representation of the appliance within said transform volume.

12. The method of claim 11 further comprising:

defining a reference plane oriented orthogonal to the rotational axis and intersecting the appliance representation;

displaying a two-dimensional view of an intersection between the three dimensional representation of the appliance and said reference plane;

wherein receiving said operator input of said desired magnitude and direction of the rotational transform to be applied comprises:

receiving an operator selection of a reference point on said reference plane; and receiving operator input of a desired rotational displacement of said reference point.

13. The method of claim 12 further comprising displaying a modified shape of said intersection in said two-dimensional view.

14. The method of claim 1 wherein applying the rotational transform comprises for each input coordinate in the input plurality of coordinates:

determining an angular displacement to be applied to the input coordinate; and generating a rotational transformation matrix for the input coordinate, said rotational transform matrix including elements operable to transform said input coordinate into an output coordinate that is angularly displaced from said input coordinate by said angular displacement about the rotational axis.

15. The method of claim 14 wherein the input plurality of coordinates are defined in a first Cartesian coordinate system and further comprising generating a modeling matrix having elements operable to transform input coordinates between said first coordinate system and a second Cartesian coordinate system, said second coordinate system having an origin located on said rotational axis, a first axis aligned with said rotational axis, and second and third axes orthogonal to said rotational axis, and wherein determining said angular displacement comprises:
- determining a corresponding coordinate of said input coordinate in said second coordinate system; and
- determining an angular displacement of each said corresponding coordinate within a plane defined by said second and third axes of said second coordinate system.

16. The method of claim 1 wherein receiving operator input identifying said coordinate location of said rotational axis comprises receiving operator input defining:
- coordinates of a three-dimensional line representing a location of the rotational axis with respect to the appliance representation;
- a location of a reference plane intersecting the appliance representation and oriented orthogonal to the three-dimensional line; and
- a location of an origin point on the reference plane through which the rotational axis passes.

17. An apparatus for applying a rotational transform to a portion of a three-dimensional representation of an appliance for a living body, the representation being defined by an input plurality of coordinates, the input plurality of coordinates representing a general shape of the appliance, the apparatus comprising a processor circuit operably configured to:
- receive operator input identifying a coordinate location of a rotational axis about which the rotational transform is to be applied;
- receive operator input of a constraint defining an extent of a transform volume within which the rotational transform is to be applied to the representation of the appliance, said constraint comprising first and second rotational constraints with respect to the rotational axis, said first and second rotational constraints defining an angular extent of said transform volume about said rotational axis;
- receive operator input of a rotational transform magnitude;
- apply the rotational transform to the portion of the representation of the appliance within the transform volume to produce an output plurality of coordinates representing a modified shape of the appliance such that the general shape of portions of the appliance outside the transform volume remain un-modified by the rotational transform; and
- store the output plurality of coordinates in a memory of the processor circuit.

18. The apparatus of claim 17 wherein said processor circuit is operably configured to generate a set of instructions operable to control a computer aided manufacturing machine to produce one of the appliance and a mold for producing the appliance in accordance with said output plurality of coordinates.

19. The apparatus of claim 17 wherein said processor circuit is operably configured to receive said operator input of said constraint by receiving operator input of at least one axial constraint limiting an extent of the transform volume in a direction along the rotational axis.

20. The apparatus of claim 19 wherein said processor circuit is operably configured to receive said operator input defining said at least one axial constraint by receiving operator input defining at least one constraint plane oriented orthogonal to the rotational axis and intersecting the appliance representation.

21. The apparatus of claim 19 wherein said processor circuit is operably configured to receive said operator input defining said at least one axial constraint by receiving operator input defining first and second spaced apart axial constraints along the rotational axis, the first and second axial constraints limiting an extent of the transform volume to between the first and second axial constraints.

22. The apparatus of claim 19 wherein said processor circuit is operably configured to:
- identify an axial blending region extending into said transform volume from said at least one axial constraint; and
- wherein said processor circuit is operably configured to apply the rotational transform by reducing a magnitude of the rotational transform within said axial blending region to cause continuity of shape between modified portions of the representation of the appliance within said transform volume and un-modified portions of the representation of the appliance outside said transform volume.

23. The apparatus of claim 22 wherein said processor circuit is operably configured to reduce said magnitude of the rotational transform by applying a rotational transform having:
- substantially zero magnitude at said axial constraint; and
- a magnitude that progressively increases with distance away from said at least one axial constraint to reach a full rotational transform magnitude beyond said axial blending region.

24. The apparatus of claim 17 wherein said processor circuit is operably configured to apply the rotational transform to said portion of the three-dimensional representation of the appliance within said transform volume by:
- identifying first and second rotational blending regions extending from said first and second rotational constraints into said transform volume; and
- wherein said processor circuit is operably configured to apply the rotational transform by reducing a magnitude of the rotational transform within said first and second rotational blending regions respectively to cause continuity of shape between modified portions of the representation of the appliance within said transform volume and un-modified portions of the representation of the appliance outside said transform volume.

25. The apparatus of claim 24 wherein said processor circuit is operably configured to reduce said magnitude of the rotational transform by applying a rotational transform having:
- substantially zero magnitude at said first and second rotational constraints; and
- a magnitude that progressively increases with rotational displacement into said transform volume to reach a full rotational transform magnitude beyond said first and second rotational blending regions respectively.

26. The apparatus of claim 24 wherein said processor circuit is operably configured to identify said first and second rotational blending regions by:
- receiving operator input of a no-blending zone located between said first and second rotational constraints, said no-blending zone defining an angular extent of the transform volume about said rotational axis within which a full magnitude of the rotational transform is to be applied, and wherein said first and second rotational blending regions respectively comprise portions of the transform volume outside said no-blending zone.

27. The apparatus of claim 17 wherein said processor circuit is operably configured to receive operator input of a desired rotational magnitude and direction of the rotational transform to be applied to said portion of the three-dimensional representation of the appliance within said transform volume.

28. The apparatus of claim 27 wherein said processor circuit is operably configured to:
define a reference plane oriented orthogonal to the rotational axis and intersecting the appliance representation;
display a two-dimensional view of an intersection between the three dimensional representation of the appliance and said reference plane;
wherein said processor circuit is operably configured to receive said operator input of said desired magnitude and direction of the rotational transform to be applied by:
receiving an operator selection of a reference point on said reference plane; and
receiving operator input of a desired rotational displacement of said reference point.

29. The apparatus of claim 28 wherein said processor circuit is operably configured to display a modified shape of said intersection in said two-dimensional view.

30. The apparatus of claim 17 wherein said processor circuit is operably configured to apply the rotational transform by:
determining an angular displacement to be applied to each input coordinate in the input plurality of coordinates; and
generating a rotational transformation matrix for the input coordinate, said rotational transform matrix including elements operable to transform said input coordinate into an output coordinate that is angularly displaced from said input coordinate by said angular displacement about the rotational axis.

31. The apparatus of claim 30 wherein the input plurality of coordinates are defined in a first Cartesian coordinate system and wherein said processor circuit is operably configured to generate a modeling matrix having elements operable to transform input coordinates between said first coordinate system and a second Cartesian coordinate system, said second coordinate system having an origin located on said rotational axis, a first axis aligned with said rotational axis, and second and third axes orthogonal to said rotational axis, and wherein said processor circuit is operably configured to determine said angular displacement by:
determining a corresponding coordinate of said input coordinate in said second coordinate system; and
determining an angular displacement of each said corresponding coordinate within a plane defined by said second and third axes of said second coordinate system.

32. The apparatus of claim 17 wherein said processor circuit is operably configured to receive operator input identifying said coordinate location of said rotational axis by receiving operator input defining:
coordinates of a three-dimensional line representing a location of the rotational axis with respect to the appliance representation;
a location of a reference plane intersecting the appliance representation and oriented orthogonal to the three-dimensional line; and
a location of an origin point on the reference plane through which the rotational axis passes.

33. A non-transitory computer readable medium encoded with codes for directing a processor circuit to apply a rotational transform to a portion of a three-dimensional representation of an appliance for a living body, the representation being defined by an input plurality of coordinates stored in a processor circuit memory, the input plurality of coordinates representing a general shape of the appliance, the codes directing the processor circuit to:
receive operator input identifying a coordinate location of a rotational axis about which the rotational transform is to be applied;
receive operator input of a constraint defining an extent of a transform volume within which the rotational transform is to be applied to the representation of the appliance, said constraint comprising first and second rotational constraints with respect to the rotational axis, said first and second rotational constraints defining an angular extent of said transform volume about said rotational axis;
receive operator input of a rotational transform magnitude;
apply the rotational transform to the portion of the representation of the appliance within the transform volume to produce an output plurality of coordinates representing a modified shape of the appliance such that the general shape of portions of the appliance outside the transform volume remain un-modified by the rotational transform; and
store the output plurality of coordinates in a memory of the processor circuit.

34. An apparatus for applying a rotational transform to a portion of a three-dimensional representation of an appliance for a living body, the representation being defined by an input plurality of coordinates stored in a processor circuit memory, the input plurality of coordinates representing a general shape of the appliance, the apparatus comprising:
means for receiving operator input identifying a coordinate location of a rotational axis about which the rotational transform is to be applied;
means for receiving operator input of a constraint defining an extent of a transform volume within which the rotational transform is to be applied to the representation of the appliance, said constraint comprising first and second rotational constraints with respect to the rotational axis, said first and second rotational constraints defining an angular extent of said transform volume about said rotational axis;
means for receiving operator input of a rotational transform magnitude;
means for applying the rotational transform to the portion of the representation of the appliance within the transform volume to produce an output plurality of coordinates representing a modified shape of the appliance such that the general shape of portions of the appliance outside the transform volume remain un-modified by the rotational transform; and
means for storing the output plurality of coordinates in the processor circuit memory.

35. The apparatus of claim 34 further comprising means for generating a set of instructions operable to control a computer aided manufacturing machine to produce one of the appliance and a mold for producing the appliance in accordance with said output plurality of coordinates.

36. The apparatus of claim 34 wherein said means for receiving said operator input of said constraint comprises means for receiving operator input of at least one axial constraint limiting an extent of the transform volume in a direction along the rotational axis.

37. The apparatus of claim 36 further comprising:
means for identifying an axial blending region extending into said transform volume from said at least one axial constraint; and
wherein said means for applying the rotational transform comprises means for reducing a magnitude of the rotational transform within said axial blending region to cause continuity of shape between modified portions of the representation of the appliance within said transform volume and un-modified portions of the representation of the appliance outside said transform volume.

38. The apparatus of claim 34 wherein said means for applying the rotational transform to said portion of the three-dimensional representation of the appliance within said transform volume comprises:
  means for identifying first and second rotational blending regions extending from said first and second rotational constraints into said transform volume; and
  wherein said means for applying the rotational transform comprises means for reducing a magnitude of the rotational transform within said first and second rotational blending regions respectively to cause continuity of shape between modified portions of the representation of the appliance within said transform volume and un-modified portions of the representation of the appliance outside said transform volume.

39. The apparatus of claim 34 wherein said means for applying the rotational transform comprises :
  means for determining an angular displacement to be applied to each input coordinate in the input plurality of coordinates; and
  means for generating a rotational transformation matrix for the input coordinate, said rotational transform matrix including elements operable to transform said input coordinate into an output coordinate that is angularly displaced from said input coordinate by said angular displacement about the rotational axis.

* * * * *